United States Patent
Park et al.

(10) Patent No.: US 9,046,470 B2
(45) Date of Patent: Jun. 2, 2015

(54) OPTICAL BIOSENSOR, BIO-SENSING SYSTEM INCLUDING THE SAME, AND METHOD OF FABRICATING THE OPTICAL BIOSENSOR

(71) Applicants: Yoon-dong Park, Osan-si (KR); Kyoung-won Na, Seoul (KR); Sung Dong Suh, Seoul (KR); Dong-mo Im, Jindo-gun (KR)

(72) Inventors: Yoon-dong Park, Osan-si (KR); Kyoung-won Na, Seoul (KR); Sung Dong Suh, Seoul (KR); Dong-mo Im, Jindo-gun (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 56 days.

(21) Appl. No.: 13/833,778

(22) Filed: Mar. 15, 2013

(65) Prior Publication Data

US 2013/0309135 A1    Nov. 21, 2013

Related U.S. Application Data

(60) Provisional application No. 61/614,705, filed on Mar. 23, 2012, provisional application No. 61/619,703, filed on Apr. 3, 2012.

(30) Foreign Application Priority Data

Nov. 2, 2012    (KR) .................. 10-2012-0123741

(51) Int. Cl.
*G01N 27/30* (2006.01)
*G01N 21/17* (2006.01)
(Continued)

(52) U.S. Cl.
CPC ........... *G01N 21/17* (2013.01); *Y10T 29/49117* (2015.01); *B01L 2200/027* (2013.01);
(Continued)

(58) Field of Classification Search
CPC .......... G01N 21/7746; G01N 21/7703; G01N 2021/0346; G01N 27/44721; G01N 15/1484; G01N 2021/7793; G01N 21/78; G01N 33/54386; G01N 31/22; G01N 31/223; G01N 33/521; G01N 33/545; G02B 2006/12138; B01L 3/5027; B01L 2300/0636; B01L 2200/10; B01L 2300/0816; B01L 2200/027; B01L 9/527; G04F 1/00; G04F 1/06; G04F 13/06; G04F 13/00; B41M 5/392; B41M 5/395; B41M 5/42; B41M 5/52; F16L 1/11; G09F 7/18; G09F 3/04; G09F 3/06; G09F 3/0295; H01B 13/344; H01B 7/368; C09D 11/50
USPC .............. 422/52, 82.05, 82.06, 82.07, 82.08, 422/82.09, 82.11, 407, 500, 501, 502, 503, 422/504, 930; 436/52, 53, 164, 165, 172, 436/174, 518, 524, 525, 526, 805, 809; 435/164, 165, 283.1, 287.1, 287.2, 435/288.7, 808, 4, 5, 7.2, 7.9
See application file for complete search history.

(56) References Cited

U.S. PATENT DOCUMENTS 7,141,414 B2    11/2006    Carpenter
8,177,720 B2    5/2012    Nanba et al.
(Continued)

FOREIGN PATENT DOCUMENTS

| JP | 2004105184 A | 4/2004 |
| JP | 2005274164 A | 10/2005 |

(Continued)

*Primary Examiner* — Dennis M White
(74) *Attorney, Agent, or Firm* — Harness, Dickey & Pierce, P.L.C.

(57) ABSTRACT

An optical biosensor including a bio-sensing unit configured to receive an optical signal and generating a sensed optical signal, the wavelength of which varies according to a result of sensing a biomaterial; and a spectrometer including a plurality of ring resonators for dividing the sensed optical signal according to a wavelength and generating a plurality of output optical signals, respectively.

32 Claims, 20 Drawing Sheets

(51) Int. Cl.
*B01L 9/00* (2006.01)
*G01N 21/77* (2006.01)
*G01N 21/03* (2006.01)
*G01N 15/14* (2006.01)
*B01L 3/00* (2006.01)
*G02B 6/12* (2006.01)
*G01N 27/447* (2006.01)

(52) U.S. Cl.
CPC .......... *B01L9/527* (2013.01); *B01L 2300/0816* (2013.01); *G01N 2021/7793* (2013.01); *G01N 2021/0346* (2013.01); *B01L 2200/10* (2013.01); *G01N 15/1484* (2013.01); *B01L 2300/0636* (2013.01); *B01L 3/5027* (2013.01); *G02B 2006/12138* (2013.01); *G01N 27/44721* (2013.01); *G01N 21/7703* (2013.01); G01N 21/7746 (2013.01)

(56) References Cited

U.S. PATENT DOCUMENTS

| | | | |
|---|---|---|---|
| 2004/0146431 A1* | 7/2004 | Scherer et al. | 422/82.05 |
| 2010/0260643 A1 | 10/2010 | Ko et al. | |
| 2011/0238382 A1 | 9/2011 | Gollier et al. | |

FOREIGN PATENT DOCUMENTS

| | | |
|---|---|---|
| JP | 2007248318 A | 9/2007 |
| JP | 2007319378 A | 12/2007 |
| JP | 2009301120 A | 12/2009 |
| KR | 101114188 B1 | 2/2012 |
| KR | 20120013821 A | 2/2012 |

* cited by examiner

OPTICAL BIOSENSOR, BIO-SENSING SYSTEM INCLUDING THE SAME, AND METHOD OF FABRICATING THE OPTICAL BIOSENSOR

CROSS-REFERENCE TO RELATED APPLICATIONS

This application claims the benefit of Korean Patent Application No. 10-2012-0123741, filed on Nov. 2, 2012, in the Korean Intellectual Property Office and claims the benefit of priority under 35 U.S.C. §119(e) to U.S. provisional application No. 61/614,705 filed Mar. 23, 2012 and 61/619,703 filed on Apr. 3, 2012, the disclosures of which are incorporated herein in their entirety by reference.

BACKGROUND

The inventive concepts relates to an optical biosensor, and more particularly, to an optical biosensor, a bio-sensing system including the optical biosensor, and a method of fabricating the optical biosensor.

Biosensors are devices that measure the concentration of an organic or inorganic material in a liquid or gaseous state. Examples of biosensors may include a piezoelectric biosensor, an optical biosensor, an electrochemical biosensor, and the like. An optical biosensor measures the concentration of a biomaterial based on an optical phenomenon that a biological factor interacts with a target material that is to be sensed.

SUMMARY

According to an aspect of the inventive concepts, there is provided an optical biosensor including a bio-sensing unit configured to sense a biomaterial by receiving an input optical signal and generating a sensed optical signal having a wavelength which varies according to the biomaterial; and a spectrometer configured to generate a plurality of output optical signals by passing the sensed optical signal through a plurality of ring resonators having different resonant wavelengths, the plurality of output optical signals having intensities that vary based on the biomaterial.

The sensed optical signal may be a signal obtained by one of extracting a resonant wavelength from a wavelength component of the input optical signal and dissipating the resonant wavelength from the input optical signal, the resonant wavelength varying according to a concentration of the biomaterial. The bio-sensing unit may include a ring resonator configured to extract the resonant wavelength from the wavelength component of the input optical signal.

The bio-sensing unit may include a first optical waveguide configured to receive the input optical signal; a ring resonator configured to extract the resonant wavelength from the wavelength component of the input optical signal, the resonant wavelength extracted via an interval between the ring resonator and the first optical waveguide; and a second optical waveguide configured to provide the resonant wavelength to the spectrometer as the sensed optical signal via an interval between the second optical waveguide and the ring resonator.

The bio-sensing unit may include an optical waveguide for receiving the input optical signal; and a ring resonator for generating the sensed optical signal by dissipating the resonant wavelength from a wavelength of the input optical signal via an interval between the ring resonator and the optical waveguide, and providing the sensed optical signal to the optical waveguide.

The bio-sensing unit may include a first optical waveguide for receiving the input optical signal; a cavity resonator for extracting the resonant wavelength from a wavelength of the input optical signal and providing the resonant wavelength as the sensed optical signal; and a second optical waveguide for receiving the sensed optical signal and providing the sensed optical sensed optical signal to the spectrometer.

The spectrometer may include a first optical waveguide for receiving the sensed optical signal; the plurality of ring resonators for extracting a plurality of resonant wavelengths from the wavelength of the sensed optical signal via intervals between the plurality of ring resonators and the first optical waveguide; and a plurality of second optical waveguides for receiving the plurality of resonant wavelengths via intervals between the plurality of second optical waveguides and the plurality of ring resonators, and providing the plurality of resonant wavelengths as the plurality of output optical signals.

The plurality of ring resonators may extract different resonant wavelengths, respectively.

Grating couplers may be located at ends of the plurality of second optical waveguides.

The spectrometer may include N ring resonators for generating N output optical signals having output wavelength components corresponding to N equal sub-bands divided from a 3 dB bandwidth of the sensed optical signal, respectively.

The bio-sensing unit and the spectrometer may be on a same semiconductor substrate.

The optical biosensor may further include a detecting unit for transforming the plurality of output optical signals into electrical signals.

The detecting unit may include a plurality of detectors for receiving the plurality of output optical signals, respectively.

The plurality of detectors may include at least one of a photodiode, a phototransistor, a time-of-flight (TOF) sensor, a complementary metal-oxide semiconductor (CMOS) sensor, and a charge-coupled device (CCD) sensor.

The bio-sensing unit, the spectrometer, and the detecting unit are formed or packaged on the same semiconductor substrate.

The optical biosensor may further include a signal processor for determining a concentration of the biomaterial based on the electrical signals output from the detecting unit.

The optical biosensor may further include an optical source for providing the input optical signal to the bio-sensing unit.

According to another aspect of the inventive concepts, there is provided an optical biosensor including a bio-sensing ring resonator configured to extract a sensed optical signal from an input optical signal, the sensed optical signal having a resonant wavelength which varies according to a concentration of a biomaterial; and a plurality of spectrum ring resonators configured to extract a plurality of output optical signals from the sensed optical signal, each output optical signal having a different wavelength.

The optical biosensor may further include a plurality of detectors for providing information to indicate intensities of the plurality of output optical signals by transforming the plurality of output optical signals into electrical signals.

According to another aspect of the inventive concepts, there is provided a bio-sensing system including a fluidic channel via which a biomaterial flows; and a biosensor chip configured to sense at least one of whether a biomaterial exists and a concentration of the biomaterial, based on optical characteristics of the biomaterial, and output an electrical signal based on the sensing. The biosensor chip including an opening adjacent to the fluidic channel; a bio-sensing unit configured to generate a sensed optical signal from an input optical signal, a wavelength of the sensed optical signal varying according to at least one of whether the biomaterial exists and the concentration of the biomaterial; and a spectrometer including a plurality of ring resonators having different resonant wavelengths. The spectrometer configured to generate a plurality of output optical signals by passing the sensed optical signal through the plurality of ring resonators, the plurality of output optical signals having intensities that vary based on the biomaterial.

The biosensor chip may further include a detecting unit for transforming the plurality of output optical signals into electrical signals based on the intensities.

The bio-sensing unit, the spectrometer, and the detecting unit are formed or packaged on the same semiconductor substrate.

According to another aspect of the inventive concepts, there is provided a method of fabricating an optical biosensor, the method including forming a cladding layer on a substrate; forming a core layer on the cladding layer; and patterning the core layer to obtain a bio-sensing ring resonator, a plurality of spectrum ring resonators, and a plurality of optical waveguides.

The plurality of optical waveguides may include a first optical waveguide for receiving an input optical signal and providing the input optical signal to the bio-sensing ring resonator as a sensed optical signal; a second optical waveguide for receiving the sensed optical signal from the bio-sensing ring resonator and providing the sensed optical signal to the plurality of spectrum ring resonators; and a plurality of third optical waveguides for receiving a plurality of output optical signals from the plurality of spectrum ring resonators.

The method may further include each of a plurality of detectors at one end of the plurality of third optical waveguides.

According to another aspect of the inventive concepts, there is provided an optical biosensor including a substrate having a biosensing unit and a spectrometer located thereon, the bio-sensing unit configured to generate a sensed optical signal based on a biomaterial, and the spectrometer configured to divide the sensed optical signal into a plurality of output optical signals that each have a different wavelength.

BRIEF DESCRIPTION OF THE DRAWINGS

Example embodiments of the inventive concepts will be more clearly understood from the following detailed description taken in conjunction with the accompanying drawings in which:

FIGS. 5A and 5B are cross-sectional views taken along line A-A' of FIG. 3, in which FIG. 5A illustrates a case where a target material is an antibody and FIG. 5B illustrates a case where a target material is deoxyribonucleic acid (DNA);

DETAILED DESCRIPTION OF THE EMBODIMENTS

Figure 1:
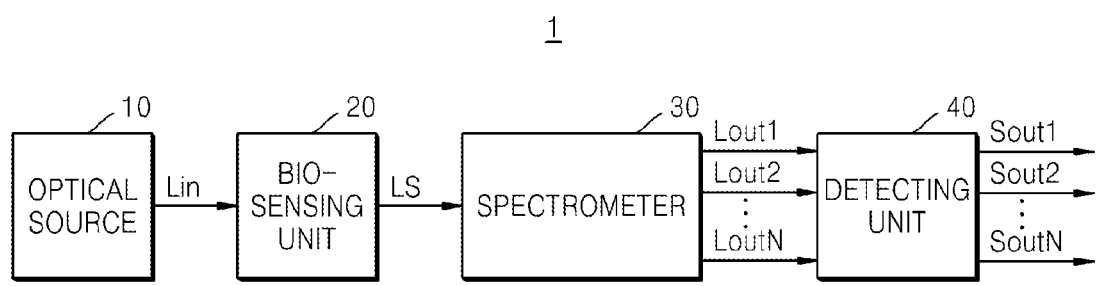
FIG. 1 is a block diagram of an optical biosensor according to an example embodiment of the inventive concepts.

Hereinafter, example embodiments of the inventive concepts will be described in detail with reference to the appended drawings. These embodiments are provided so that this disclosure will be thorough and complete, and will fully convey the scope of the inventive concepts to those of ordinary skilled in the art. Thus, the inventive concepts may be embodied in many different forms and should not be construed as limited to the Example embodiments set forth herein. In the drawings, the same reference numerals denote the same elements and the lengths and sizes of layers and regions may be exaggerated for clarity.

The terminology used herein is for the purpose of describing particular embodiments only and is not intended to be limiting of the inventive concepts. As used herein, the singular forms 'a', 'an', and 'the' are intended to include the plural forms as well, unless the context clearly indicates otherwise. It will be further understood that the terms 'comprise' and/or 'include' when used in this specification, specify the presence of stated features, integers, steps, operations, elements, and/or components, but do not preclude the presence or addition of one or more other features, integers, steps, operations, elements, components, and/or groups thereof.

It will be understood that, although the terms 'first', 'second', 'third', etc., may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the inventive concepts.

Unless otherwise defined, all terms (including technical and scientific terms) used herein have the same meaning as commonly understood by one of ordinary skill in the art to which the inventive concepts belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

As used herein, the term "and/or" includes any and all combinations of one or more of the associated listed items. Expressions such as "at least one of," when preceding a list of elements, modify the entire list of elements and do not modify the individual elements of the list.

FIG. 1 is a block diagram of an optical biosensor 1 according to an example embodiment of the inventive concepts. Referring to FIG. 1, the optical biosensor 1 may include a bio-sensing unit 20, a spectrometer 30, and a detecting unit 40. The optical biosensor 1 may further include an optical source 10. The optical biosensor 1 may sense whether a biomaterial exists or a concentration of the biomaterial, based on an optical phenomenon that occurs due to interactions of biomaterials, and particularly, combining of a target material, e.g., a target deoxyribonucleic acid (DNA) or an antigen, and a probe material, e.g., a probe DNA or an antibody.

The optical source 10 may generate an input optical signal Lin and provide the input optical signal Lin to the bio-sensing unit 20. The bio-sensing unit 20 may receive the input optical signal Lin and generate a sensed optical signal Ls, the wavelength of which varies according to a result of sensing the biomaterial. Specifically, the sensed optical signal Ls may be an optical signal obtained by extracting a resonant wavelength that varies according to the concentration of the biomaterial from a wavelength component of the input optical signal Lin or may be an optical signal obtained by dissipating the resonant wavelength from the input optical signal Lin.

The spectrometer 30 may include a plurality of ring resonators (not shown). The plurality of ring resonators may generate a plurality of output optical signals Lout1 to LoutN by dividing the sensed optical signal Ls according to a wavelength, respectively. The detecting unit 40 may include a plurality of photo detectors (not shown) that may transform the plurality of output optical signals Lout1 to LoutN into electrical signals Sout1 to SoutN, respectively.

According to an example embodiment of the inventive concepts, the bio-sensing unit 20 and the spectrometer 30 may be formed or packaged on the same substrate. According to another example embodiment of the inventive concepts, the bio-sensing unit 20, the spectrometer 30, and the detecting unit 40 may be formed or packaged on the same substrate. According to another example embodiment of the inventive concepts, the optical source 10, the bio-sensing unit 20, the spectrometer 30, and the detecting unit 40 may be formed or packaged on the same substrate.

Generally optical biosensors determine the concentration of a biomaterial by analyzing a wavelength of an optical signal obtained by sensing the biomaterial based the optical characteristics. Thus, conventional optical biosensors require, for example, a separate spectrometer to analyze the wavelength of the optical signal. In contrast, according to example embodiments of the inventive concepts, in the optical biosensor 1, the spectrometer 30 is realized using the plurality of ring resonators and may thus be integrated with another element of the optical biosensor 1, e.g., the bio-sensing unit 20. Thus, the optical biosensor 1 may be fabricated without additional equipment, e.g., a spectrometer, thereby manufacturing the optical biosensor 1 to be compact. Accordingly, the optical biosensor 1 may be operated together with a portable smart device or the like.

Figure 2:
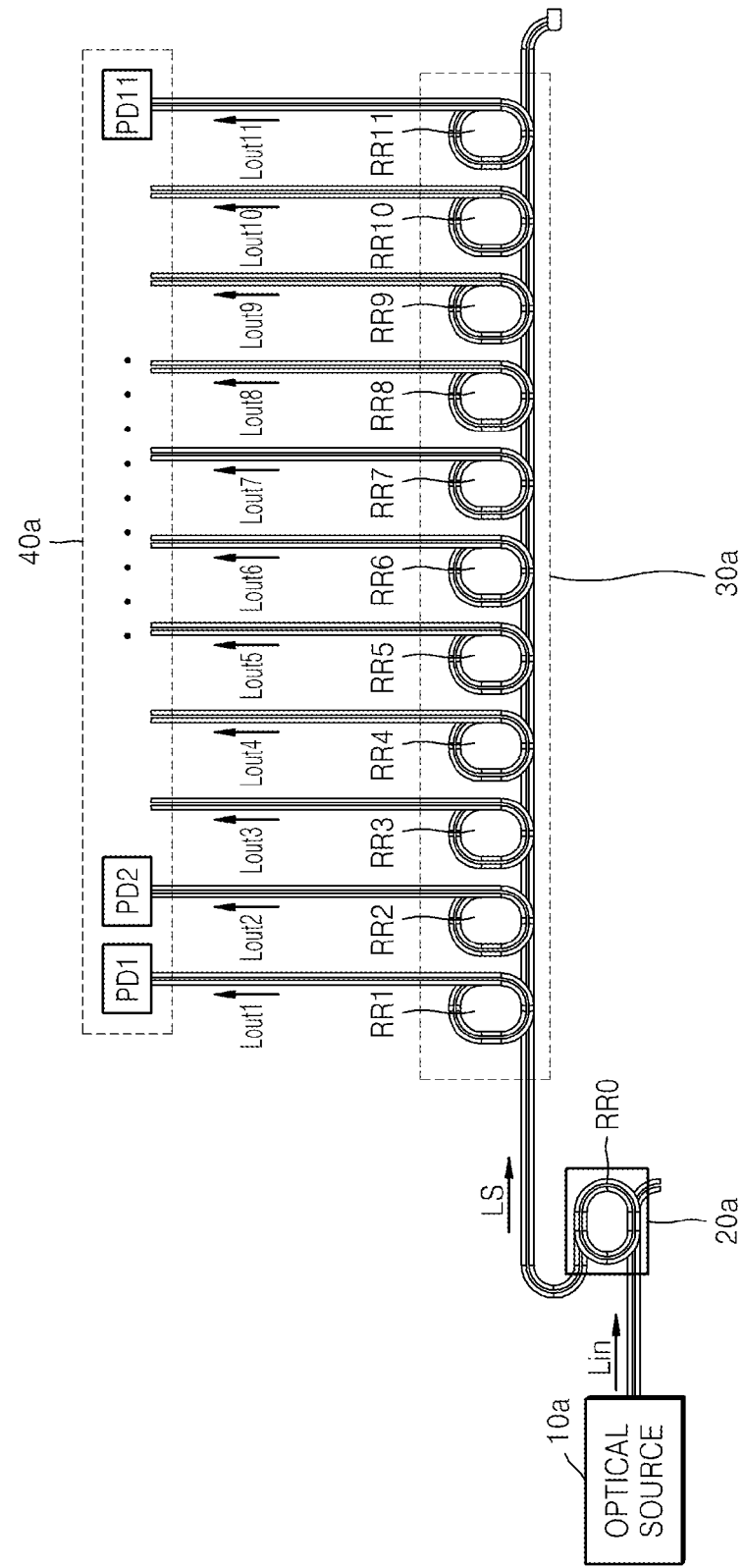
FIG. 2 specifically illustrates an example of the blocks of the block diagram of the optical biosensor of FIG. 1.

FIG. 2 specifically illustrates an optical biosensor 1a that is an example of the optical biosensor of FIG. 1.

Referring to FIG. 2, the optical biosensor 1a may include an optical source 10a, a bio-sensing unit 20a, a spectrometer 30a, and a detecting unit 40a.

The optical source 10a may generate an input optical signal Lin and provide the input optical signal Lin to the bio-sensing unit 20a. Specifically, the input optical signal Lin may include a wavelength component that is within a desired (or, alternatively a predetermined) range, e.g., a wavelength component ranging from several tens of nanometers to several hundreds of nanometers. For example, 3 dB wavelengths of the input optical signal Lin may be 845 nm and 855 nm. In this case, a 3 dB bandwidth or full width at half maximum (FWHM) of the input optical signal Lin may be 10 nm. However, the inventive concepts are not limited thereto, and a waveform and wavelength range of the input optical signal Lin may be set to other values.

According to an example embodiment of the inventive concepts, the optical source 10a may be an amplified spontaneous emission (ASE) device or a superluminescent light-emitting diode (SLED). According to another example embodiment of the inventive concepts, the optical source 10a may include a wavelength controller (not shown) and a wavelength varying optical source (not shown). The wavelength varying optical source may be, for example, a distributed feedback laser diode (DFD).

The bio-sensing unit 20a may generate a sensed optical signal Ls, the wavelength of which varies according to whether a biomaterial exists or the concentration of the biomaterial, from the input optical signal Lin. Specifically, the sensed optical signal Ls may be an optical signal obtained by extracting a resonant wavelength corresponding to the concentration of the biomaterial from a wavelength component of the input optical signal Lin. According to the current embodiment, the bio-sensing unit 20a may include a ring resonator RR0 for extracting the resonant wavelength component from the wavelength component of the input optical signal Lin. The structure of the bio-sensing unit 20a will be described in detail with reference to FIGS. 3 to 6 below.

The spectrometer 30a may include a plurality of ring oscillators RR1 to RR11. The plurality of ring oscillators RR1 to RR11 may generate a plurality of output optical signals Lout1 to Lout11 by dividing the sensed optical signal Ls according to a wavelength, respectively. In the current embodiment, eleven ring oscillators RR1 to RR11 are included in the spectrometer 30a, but the number of ring oscillators that may be included in the spectrometer 30a may vary according to embodiments of the inventive concepts. The structure of the spectrometer 30a will be described in detail with reference to FIGS. 7 to 12 below.

The detecting unit 40a may include a plurality of photo detectors PD1 to PD11. The plurality of photo detectors PD1 to PD11 may transform the plurality of output optical signals Lout11 to Lout11 into electrical signals Sout1 to Sout11, respectively (not shown). The plurality of photo detectors PD 1 to PD 11 may be connected to the plurality of ring oscillators RR1 to RR11, respectively. The number of photo detectors PD1 to PD11 may correspond to that of ring oscillators RR1 to RR1. For example, the plurality of photo detectors PD1 to PD11 may include a photodiode, a phototransistor, a charge-coupled device (CCD) image sensor, a complementary metal-oxide semiconductor (CMOS) image sensor, a time-of-flight (TOF) sensor, etc.

Figure 3:
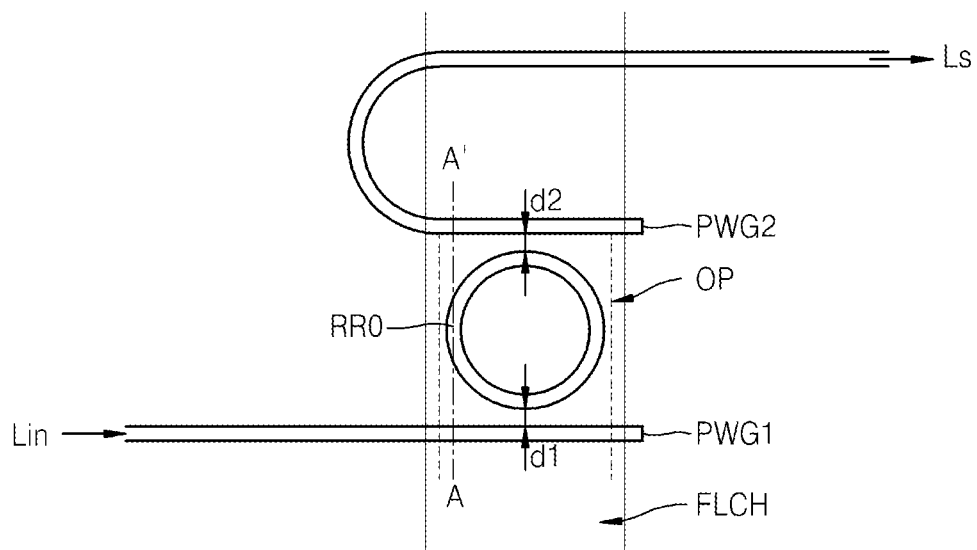
FIG. 3 specifically illustrates an expanded view of a bio-sensing unit included in the optical biosensor of FIG. 2.

FIG. 3 specifically illustrates the bio-sensing unit 20a of FIG. 2.

Referring to FIG. 3, the bio-sensing unit 20a may include a first optical waveguide PWG1, a ring resonator RR0, and a second optical waveguide PWG2. A fluidic channel FLCH may be disposed above the first optical waveguide PWG1, the ring resonator RR0, and the second optical waveguide PWG2. An opening OP via which the ring resonator RR0 is exposed in the fluidic channel FLCH may be formed above the ring resonator RR0. The first and second optical waveguides PWG1 and PWG2 may be straight-line type optical waveguides, and the ring resonator RR0 may an optical waveguide having a circular shape or a race track shape.

The ring resonator RR0 may be spaced from the first optical waveguide PWG1 by a first interval d1, and the ring resonator RR0 may be spaced from the second optical waveguide PWG2 by a second interval d2. According to an example embodiment of the inventive concepts, the ring resonator RR0 may be horizontally spaced from the first optical waveguide PWG1 by the first interval d1 and may be horizontally spaced from the second optical waveguide PWG2 by the second interval d2. According to another example embodiment of the inventive concepts, the ring resonator RR0 may be vertically spaced from the first optical waveguide PWG1 by the first interval d1 and may be vertically spaced from the second optical waveguide PWG2 by the second interval d2.

Figure 4A:
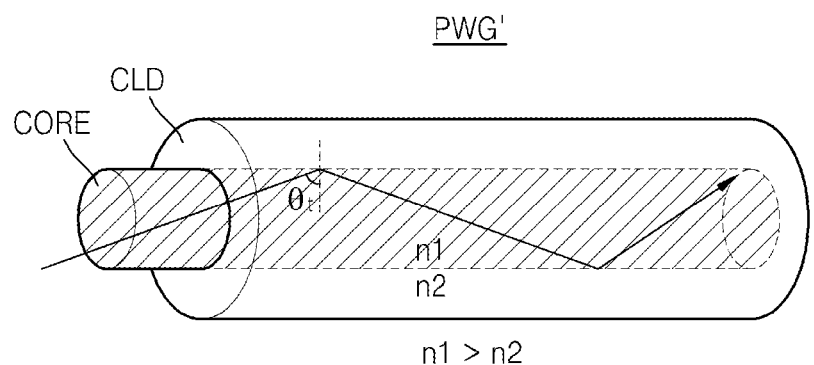
FIGS. 4A and 4B illustrate examples of optical waveguides included in a bio-sensing unit of FIG. 3.
Figure 4B:
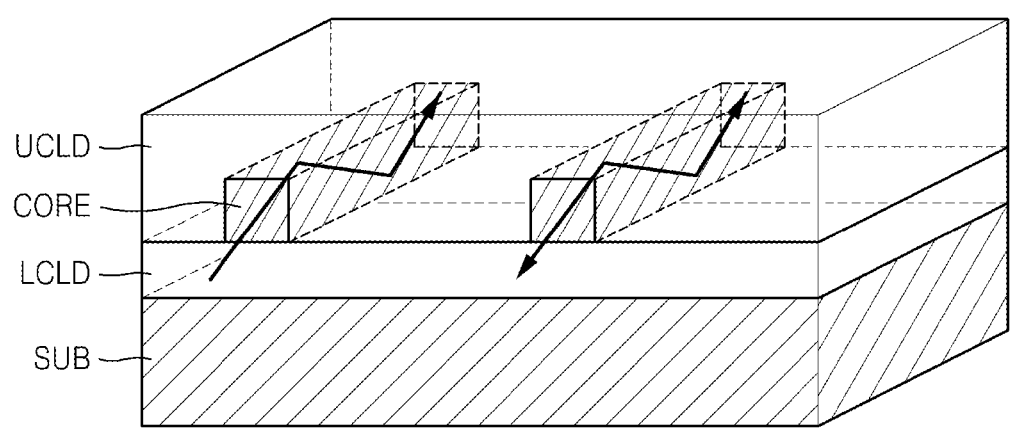

FIGS. 4A and 4B illustrate optical waveguides PWG' and PWG" that are examples of the first and second optical waveguides PWG1 and PWG2 included in the bio-sensing unit 20a of FIG. 3.

Referring to FIG. 4A, the optical waveguide PWG' may include a core layer CORE that transmits an optical signal, and a cladding layer CLD that surrounds the core layer CORE. A refractive index n1 of the core layer CORE is higher than a refractive index n2 of the cladding layer CLD. Thus, when an optical signal is incident on the core CORE at an angle θt that is greater than a threshold value, the optical signal may be totally reflected to not be radiated outside the core layer CORE and to travel within the core layer CORE while being bound within the core layer CORE.

Referring to FIG. 4B, the optical waveguide PWG" may be embodied as a silicon waveguide formed on a semiconductor substrate SUB. That is, a lower cladding layer LCLD may be formed on the semiconductor substrate SUB, a core layer CORE may be formed on the lower cladding layer LCLD, and an upper cladding layer UCLD may be formed to surround the core layer CORE. However, the inventive concepts are not limited thereto, and the structure of the optical waveguide PWG", i.e., the order in which these layers are formed and the shapes of these layers, may be determined variously.

The core layer CORE may each include silicon (Si) or a silicon-based compound, e.g., a silicon nitride (SiN). The lower cladding layer LCLD and the upper cladding layer UCLD may each include an oxide (Ox). A refractive index of the silicon (Si) is about 3.5 and a refractive index of the oxide (Ox) is about 1.4. Thus, the refractive indexes of the core layer CORE are higher than those of the lower and upper cladding layers LCLD and UCLD. Accordingly, when an optical signal is incident on the core layer CORE at an angle that is greater than the threshold value, total reflection may occur at boundaries among the core layer CORE and the lower and upper cladding layers LCLD and UCLD and the optical signal may thus be transmitted via the core layer CORE.

Referring back to FIG. 3, a wavelength satisfying a resonating condition of the ring resonator RR0, i.e., a resonant wavelength λr, of a wavelength of the input optical signal Lin that is supplied from the optical source 10 and is totally reflected to travel within the first optical waveguide PWG1, is transferred to the ring resonator RR0. Then, the resonant wavelength λr is transmitted via the ring resonator RR0, is transferred to the second optical waveguide PWG2, and is then output as the sensed optical signal Ls.

Thus, the sensed optical signal Ls generated by the bio-sensing unit 20a is an optical signal obtained by extracting the resonant wavelength λr from the input optical signal Lin. In this case, the resonant wavelength λr may vary according to the concentration of a biomaterial sensed by the bio-sensing unit 20a. Thus, a wavelength component of the sensed optical signal Ls may vary according to the concentration of the biomaterial.

More specifically, the opening OP is formed above the ring resonator RR0, via which the ring resonator RR0 may contact an external material, e.g., a biomaterial to be sensed. After a semiconductor device or circuit is formed on a semiconductor substrate, a passivation layer may be formed to protect the semiconductor device or circuit against an external material. In this case, the opening OP may be formed by not applying a passivation material onto the ring resonator RR0. A fluid or gas containing a biomaterial may flow via the fluidic channel FLCH that is disposed outside the optical biosensor 1 and contacts the opening OP, and may contact the ring resonator RR0 via the opening OP.

Figure 5A:
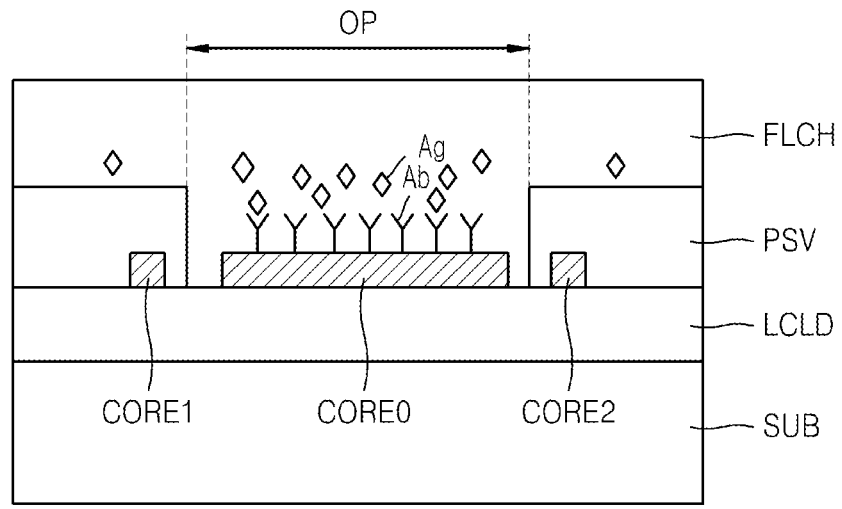
Figure 5B:
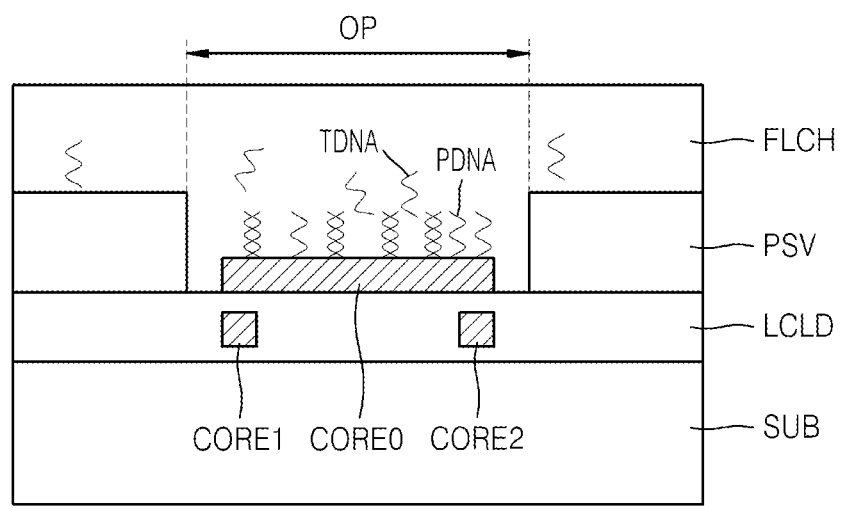

FIGS. 5A and 5B are cross-sectional views taken along line A-A' of FIG. 3, in which FIG. 5A illustrates a case where a target material is an antibody and FIG. 5B illustrates a case where a target material is DNA Referring to FIG. 5A, a core layer CORE1, a core layer CORE2, and a core layer CORE0 of the respective first optical waveguide PWG1, the second optical waveguide PWG2, and the ring resonator RR0 of FIG. 3 may be horizontally formed on the same layer. In this case, the ring resonator RR0 may be horizontally spaced from the first and second optical waveguides PWG1 and PWG2 by a desired (or, alternatively a predetermined) interval. A passivation layer PSV may be formed on the first and second optical waveguides PWG1 and PWG2, and an opening OP may be formed above the ring resonator RR0 without the passivation layer PSV.

Referring to FIG. 5B, the core layers CORE1 and CORE2 of the first and second optical waveguides PWG1 and PWG2 may be formed on a lower layer, e.g., in a lower cladding layer LCLD, and the core layer CORE0 of the ring resonator RR0 may be formed on an upper layer, e.g., on the lower cladding layer LCLD. As described above, the core layers CORE1 and CORE2 of the first and second optical waveguides PWG1 and PWG2, and the core layer CORE0 of the ring resonator RR0 may be vertically formed on different layers. In this case, the ring resonator RR0 may be vertically spaced from the first and second optical waveguides PWG1 and PWG2 by a desired (or, alternatively a predetermined) interval.

Referring to FIGS. 5A and 5B, a biomaterial that is to be measured, that is, receptors of a target material, is fixed onto the core layer CORE0 of the ring resonator RR0. The receptors may be fixed onto the core layer CORE0 of the ring resonator RR0 according to a biological or physiochemical method. Referring to FIG. 5A, the target material is an antigen (Ag) and the receptors are thus antibody (Ab). Referring to FIG. 5B, the target material is DNA (TDNA), and the receptors are thus probe DNA (PDNA).

When the receptors (Ab, PDAN) are combined with the target material, i.e., the biomaterial (Ag, TDNA), an effective refractive index of the core layer CORE0 of the ring resonator RR0 may change and a resonant wavelength $\lambda r$ of the ring resonator RR0 may thus change according to the effective refractive index of the core layer CORE0. The resonant wavelength $\lambda r$ may be expressed by Equation 1 below.

$$\lambda r = neff 2\pi R m/, \quad \text{[Equation 1]}$$

wherein 'neff' denotes the effective refractive index, 'R' denotes a radius of the ring resonator RR0, and 'm' denotes an integer. Referring to Equation 1, the resonant wavelength $\lambda r$ is proportional to the effective refractive index neff. Thus, when the effective refractive index neff increases or decreases, the resonant wavelength $\lambda r$ of the ring resonator RR0 may also increase or decrease.

For example, if the effective refractive index and resonant wavelength $\lambda r$ of the ring resonator RR0 are n0 and $\lambda 0$ before the receptors (Ab, PDNA) and the biomaterial (Ag, TDNA) are combined, then the effective refractive index of the ring resonator RR0 may increase to n1, n2, n3, . . . and the resonant wavelength $\lambda r$ of the ring resonator RR0 may change to $\lambda 0$, $\lambda 2$, $\lambda 3$, . . . when the receptors (Ab, PDNA) and the biomaterial (Ag, TDNA) are combined. A degree to which the receptors (Ab, PDNA) and the biomaterial (Ag, TDNA) are combined may vary according to the concentration of the biomaterial (Ag, TDNA). Thus, the resonant wavelength $\lambda r$ may vary according to the concentration of the biomaterial (Ag, TDNA).

Figure 6A:
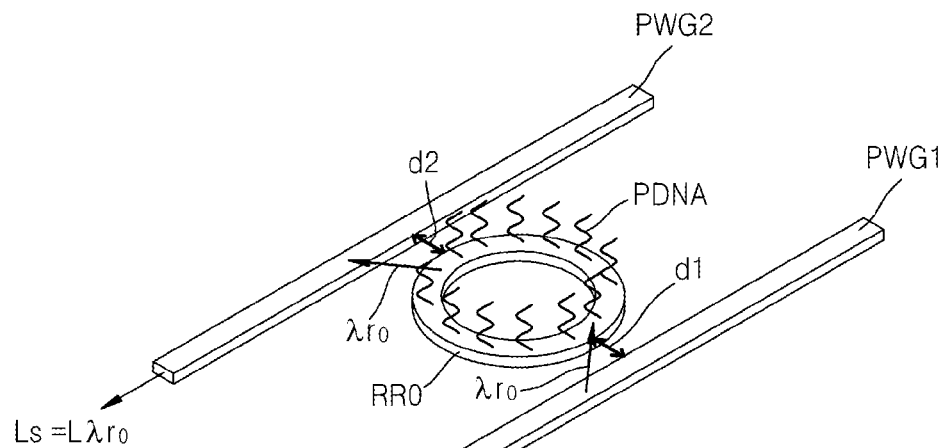
FIG. 6A illustrates a state in which a target material and a probe material have yet to be combined in the bio-sensing unit of FIG. 3.
Figure 6B:
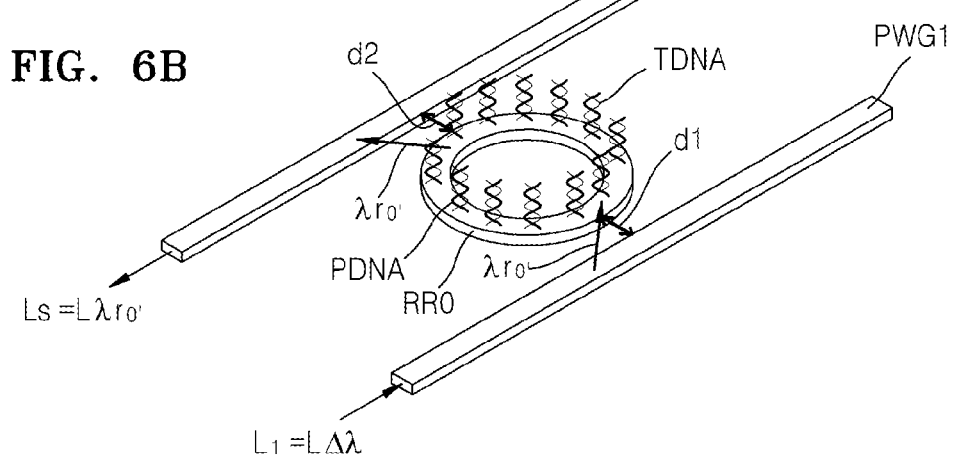
FIG. 6B illustrates a state in which the target material and the probe material have been combined in the bio-sensing unit of FIG. 3.
Figure 6C:
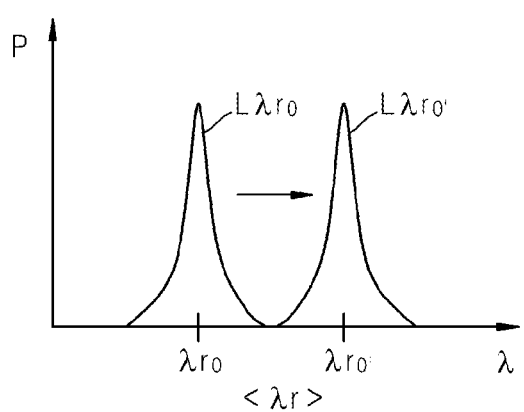
FIG. 6C is a graph illustrating wavelengths of a sensed optical signal in FIGS. 6A and 6B.

FIG. 6A illustrates a case where a target material and a probe material have yet to be combined in the bio-sensing unit 20a of FIG. 3. FIG. 6B illustrates a case where the target material and the probe material have been combined in the bio-sensing unit 20a of FIG. 3. FIG. 6C is a graph illustrating wavelengths of a sensed optical signal Ls in FIGS. 6A and 6B.

Referring to FIG. 6A, when an input optical signal Lin having a wavelength $\Delta\lambda$ of a desired (or, alternatively a predetermined) bandwidth is incident on a first optical waveguide PWG1, the input optical signal Lin travels within the first optical waveguide PWG1. In this case, a resonant wavelength $\lambda r0$ of the wavelength $\Delta\lambda$ of the desired (or, alternatively a predetermined) bandwidth is transferred to a ring resonator RR0 via an interval d1 between the first optical waveguide PWG1 and the ring resonator RR0. Also, the resonant wavelength $\lambda r0$ is transferred to a second optical waveguide PWG2 via an interval d2 between the ring resonator RR0 and the second optical waveguide PWG2, and is then output as the sensed optical signal Ls. In this case, the resonant wavelength $\lambda r$ of the ring resonator RR0 is $\lambda r0$ when a PDNA and a TDNA are not combined.

Referring to FIG. 6B, when the PDNA and the TDNA are combined, the refractive index of the ring resonator RR0 changes, thus changing the resonant wavelength from $\lambda r0$ to $\lambda r0'$. In this case, the refractive index of the ring resonator RR0 may vary according to the concentration of the TDNA, thereby changing the resonant wavelength.

Referring to FIG. 6C, when the resonant wavelength changes from $\lambda r0$ to $\lambda r0'$ due to combining the PDNA and the TDNA, the wavelength of the sensed optical signal Ls changes from $L\lambda r0$ to $L\lambda r0'$.

Figure 7:
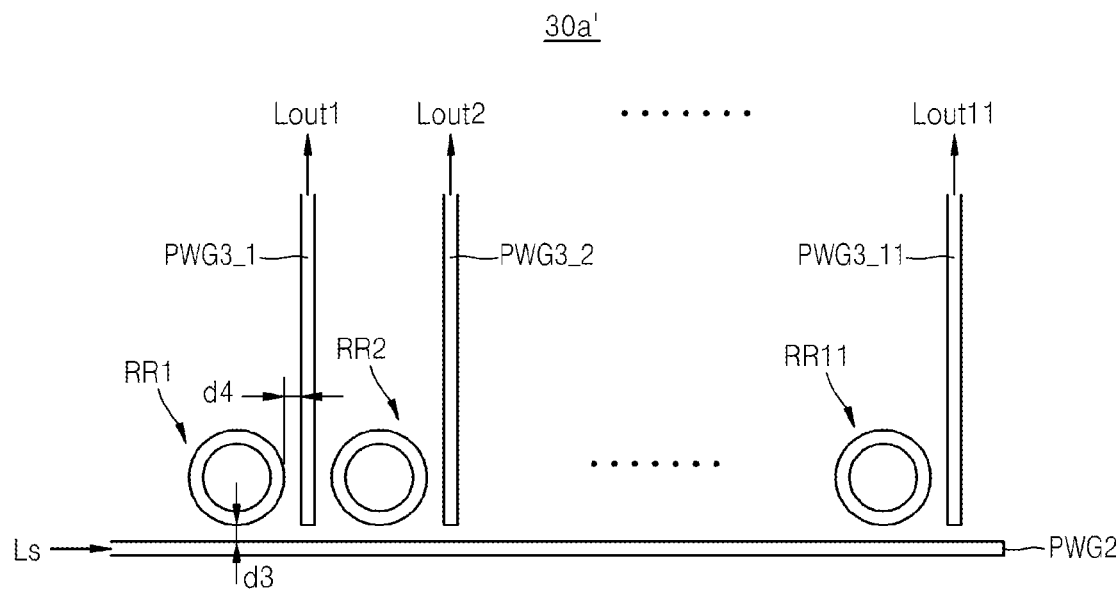
FIG. 7 specifically illustrates an example of a spectrometer included in the optical biosensor of FIG. 2 according to an example embodiment of the inventive concepts.

FIG. 7 specifically illustrates a spectrometer 30a' that is another example of the spectrometer 30 of FIG. 2.

Referring to FIG. 7, the spectrometer 30a' may include a second optical waveguide PWG2, a plurality of ring oscillators RR1 to RR11, and a plurality of third optical waveguides PWG3_1 to PWG3_11. In detail, the spectrometer 30a' may include N ring oscillators RR1 to RR11 that generate N output optical signals having output wavelength components corresponding to N equal parts divided from a 3 dB bandwidth of a sensed optical signal Ls, respectively. In the current embodiment, N may be '11', but the inventive concepts are not limited thereto and the number of ring resonators may be set to other values.

The second optical waveguide PWG2 and the plurality of third optical waveguides PWG3_1 to PWG3_11 may be straight-line type optical waveguides, and the plurality of ring oscillators RR1 to RR11 may be optical waveguides each having a circular or race track shape. In the current embodiment, the plurality of third optical waveguides PWG3_1 to PWG3_11 may be disposed perpendicular to the second optical waveguide PWG2.

The plurality of ring oscillators RR1 to RR11 may be spaced from the second optical waveguide PWG2 by a third interval d3. However, according to another example embodiment of the inventive concepts, the plurality of ring oscillators RR1 to RR11 may be spaced from the second optical waveguide PWG2 by different intervals, respectively. Also, the plurality of ring oscillators RR1 to RR11 may be spaced from the corresponding third optical waveguides PWG3_1 to PWG3_11 by a fourth interval d4, respectively. However, according to another example embodiment of the inventive concepts, the plurality of ring oscillators RR1 to RR11 may be spaced from the corresponding third optical waveguides PWG3_1 to PWG3_11 by different intervals, respectively.

According to an example embodiment of the inventive concepts, the plurality of ring oscillators RR1 to RR11 may be horizontally spaced from the second optical waveguide PWG2 by the third interval d3, and may be horizontally spaced from the corresponding third optical waveguides PWG3_1 to PWG3_11 by the fourth interval d4. According to another example embodiment of the inventive concepts, the plurality of ring oscillators RR1 to RR11 may be vertically spaced from the second optical waveguide PWG2 by the third interval d3, and may be vertically spaced from the corresponding third optical waveguides PWG3_1 to PWG3_11 by the fourth interval d4, respectively.

A plurality of ring resonators, i.e., the first to eleventh ring oscillators RR1 to RR11, may have different resonant wavelengths. For example, a resonant wavelength $\lambda r1$ of the first ring resonator RR1 may be the smallest, and a resonant wavelength $\lambda r11$ of the eleventh ring resonator RR11 may be the largest. In this case, the difference between resonant wavelengths of every two adjacent ring resonators among the first to eleventh ring oscillators RR1 to RR11 may be the same.

Figure 8:
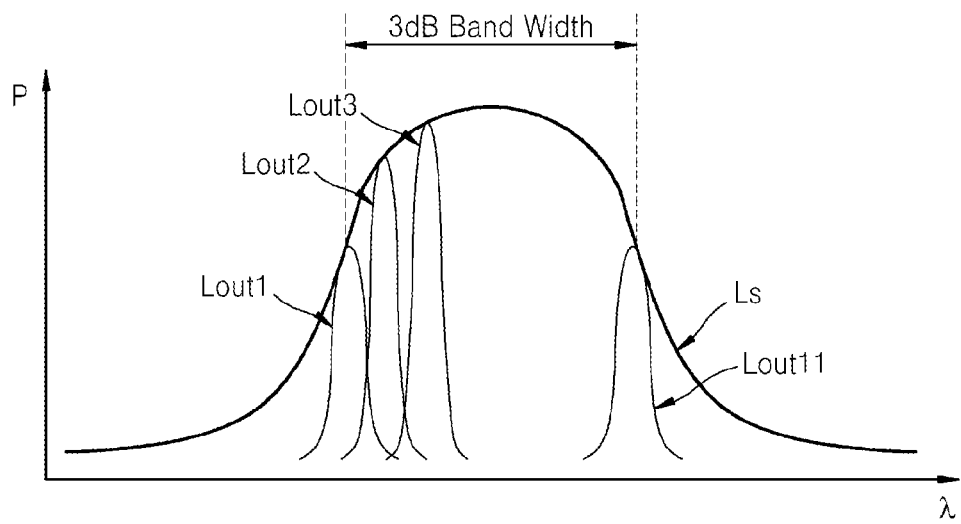
FIG. 8 is a graph illustrating spectrums of a sensed optical signal and a plurality of output optical signals in the spectrometer of FIG. 7.

FIG. 8 is a graph illustrating spectrums of a sensed optical signal Ls and a plurality of output optical signals Lout1 to Lout11 in the spectrometer 30a' of FIG. 7.

Referring to FIG. 8, the spectrometer 30a' may generate the plurality of output optical signals Lout1 to Lout11 by dividing the sensed optical signal Ls based on a 3 dB bandwidth of the sensed optical signal Ls. Specifically, the spectrometer 30a' may generate N output optical signals Lout1 to Lout11 by dividing the 3 dB bandwidth of the sensed optical signal Ls into (N−1) equal sub-bands. A waveform corresponding to the 3 dB bandwidth of the sensed optical signal Ls may be obtained by connecting Gaussian peaks of the N output optical signals Lout1 to Lout11.

In the current embodiment, 3 dB wavelengths of the sensed optical signal Ls are 849.75 nm to 850.25 nm, and a 3 dB bandwidth of the sensed optical signal Ls is 0.5 nm. Here, N may be '11'. In this case, the spectrometer 30a' may generate first to eleventh output optical signals Lout1 to Lout11, the distances between the peaks are 0.05 nm by dividing 0.5 nm that is the 3 dB bandwidth of the sensed optical signal Ls by 10 (i.e., N−1). In this case, the peak of the first output optical signal Lout1 may be 849.75 nm, the peak of the second output optical signal Lout2 may be 849.80 nm, and the peak of the eleventh output optical signal Lout11 may be 850.25 nm.

Figure 9:
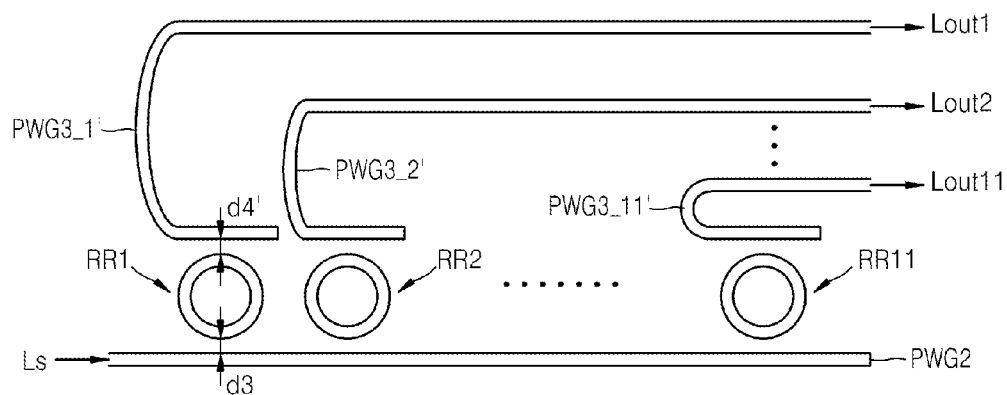
FIG. 9 specifically illustrates another example of the spectrometer included in the optical biosensor of FIG. 2 according to an example embodiment of the inventive concepts.

FIG. 9 specifically illustrates a spectrometer 30a'' that is another example of the spectrometer 30 of FIG. 2 according to the inventive concepts.

Referring to FIG. 9, the spectrometer 30a'' may include a second optical waveguide PWG2, a plurality of ring oscillators RR1 to RR11, and a plurality of third optical waveguides PWG3_1' to PWG3_11'. Specifically, the spectrometer 30a'' may include N ring resonators RR1 to RR11 that generate N output optical signals having output wavelength components corresponding to N equal sub-bands divided from a 3 dB bandwidth of a sensed optical signal Ls, respectively. In the current embodiment, 'N' may be '11', but the inventive concepts are not limited thereto and the number of ring resonators may be set to other values.

The second optical waveguide PWG2 and the plurality of third optical waveguides PWG3_1' to PWG3_11' may be straight-line type optical waveguides, and the plurality of ring oscillators RR1 to RR11 may be optical waveguides each having a circular or race track shape. In the current embodiment, the plurality of third optical waveguides PWG3_1' to PWG3_11' may be disposed parallel to the second optical waveguide PWG2.

The plurality of ring oscillators RR1 to RR11 may be spaced from the second optical waveguide PWG2 by a third interval d3. However, according to another example embodiment of the inventive concepts, the plurality of ring oscillators RR1 to RR11 may be spaced from the second optical waveguide PWG2 by different intervals. Otherwise, the plurality of ring oscillators RR1 to RR11 may be spaced from the corresponding third optical waveguides PWG3_1' to PWG3_11' by a fourth interval d4'. However, according to another example embodiment of the inventive concepts, the plurality of ring oscillators RR1 to RR11 may be spaced from the corresponding third optical waveguides PWG3_1' to PWG3_11' by different intervals.

According to one embodiment of the inventive concepts, the plurality of ring oscillators RR1 to RR11 may be horizontally spaced from the second optical waveguide PWG2 by the third interval d3 and may be horizontally spaced from the corresponding third optical waveguides PWG3_1' to PWG3_11' by the fourth interval d4. According to another example embodiment of the inventive concepts, the plurality of ring oscillators RR1 to RR11 may be vertically spaced from the second optical waveguide PWG2 by the third interval d3 and may be vertically spaced from the corresponding third optical waveguides PWG3_1' to PWG3_11' by the fourth interval d4.

The plurality of ring resonators, i.e., first to eleventh ring oscillators RR1 to RR11, may have different resonant wavelengths. For example, a resonant wavelength λr1 of the first ring resonator RR1 may be the smallest, and a resonant wavelength λr11 of the eleventh ring resonator RR11 may be the largest. In this case, the differences between resonant wavelengths of every two adjacent ring resonators among the first to eleventh ring resonators RR1 to RR11 may be the same. Spectrums of a plurality of output optical signals Lout1 to Lout11 may be the same as those of the plurality of output optical signals Lout1 to Lout11 illustrated in FIG. 8 and are thus not described again here.

Figure 10:
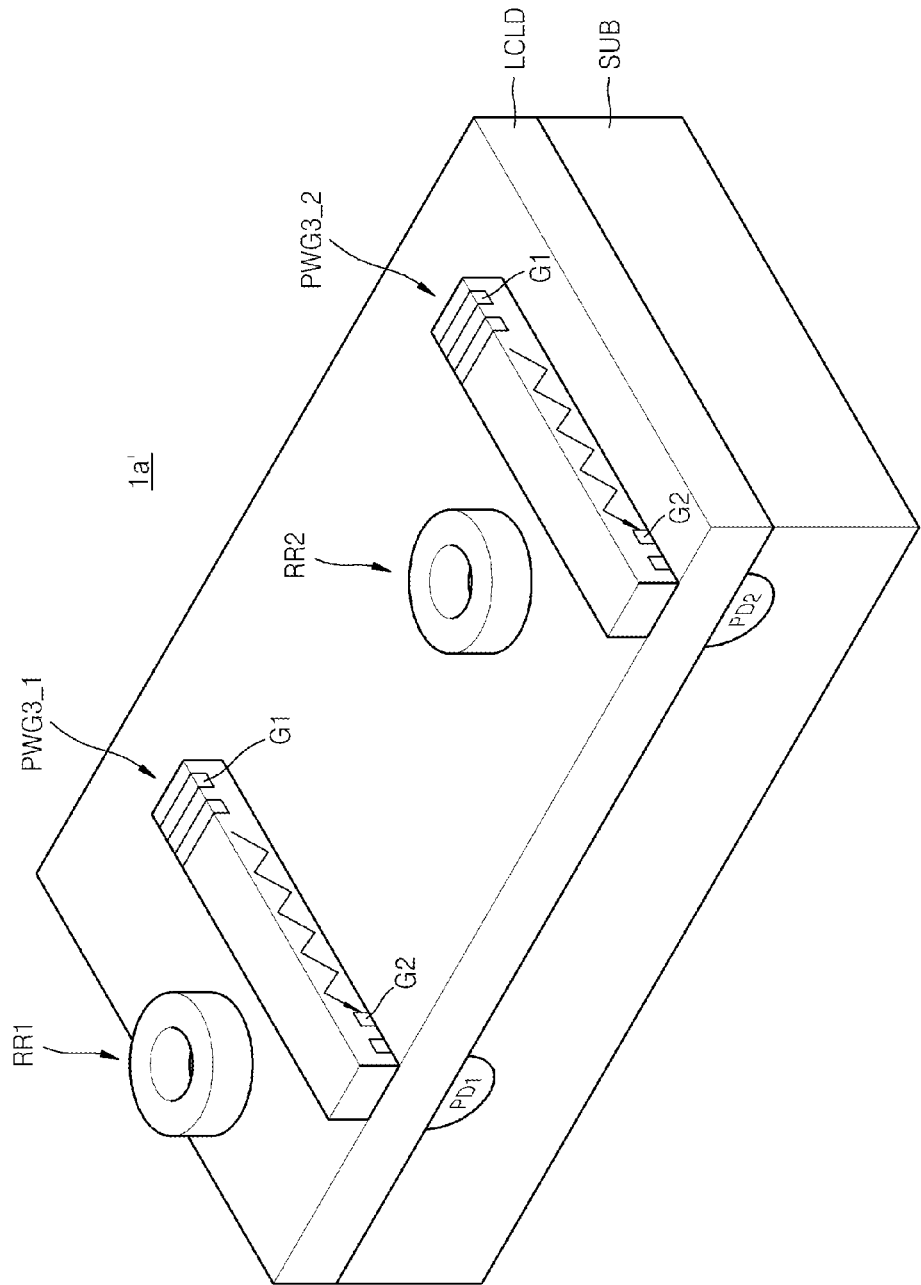
FIG. 10 is a perspective view of a part of an optical biosensor including the spectrometer of FIG. 7, according to another example embodiment of the inventive concepts.

FIG. 10 is a perspective view of a part of an optical biosensor 1a' including the spectrometer 30a' of FIG. 7, according to another example embodiment of the inventive concepts.

Referring to FIG. 10, in the optical biosensor 1a', a plurality of photo detectors, e.g., photodiodes PD1 and PD2, may be disposed on an upper region of a substrate SUB, a lower cladding layer LCLD may be disposed on the upper region of a substrate SUB, and core layers of a plurality of ring oscillators RR1 and RR2 and core layers of a plurality of third optical waveguides PWG3_1 and PWG3_2 may be disposed on the lower cladding layer LCLD. Hereinafter, for convenience of explanation, the core layers of the plurality of ring oscillators RR1 and RR2 will be referred to as the plurality of ring oscillators RR1 and RR2, and the core layers of the plurality of third optical waveguides PWG3_1 and PWG3_2 will be referred to as the plurality of third optical waveguides PWG3_1 and PWG3_2.

For convenience of explanation, the first and second optical waveguides PWG1 and PWG2 and the ring resonator RR0 included in the bio-sensing unit 20a of FIG. 3 are not illustrated in FIG. 10. According to an example embodiment of the inventive concepts, the second optical waveguide PWG2 may be disposed perpendicular to the plurality of third optical waveguides PWG3_1 and PWG3_2. However, the inventive concepts are not limited thereto, and the second optical waveguide PWG2 and the plurality of third optical waveguides PWG3_1 and PWG3_2 may be arranged in other ways.

In the current embodiment, grating couplers G1 and G2 may be formed at ends of the plurality of third optical waveguides PWG3_1 and PWG3_2, respectively. The grating couplers G1 and G2 may be manufactured by forming gratings, i.e., grids, on end portions of the plurality of third optical waveguides PWG3_1 and PWG3_2. The grating couplers G1 and G2 are capable of transmitting/receiving light using the feature of light that diffracts at a grid, and filtering light by controlling the distance between grids.

The sizes of the grids formed to manufacture the grating couplers G1 and G2, i.e., the intervals of the grids, may be determined by the width w of light incident thereon and a wave vector (k-vector). Thus, by appropriately forming grids to manufacture the grating couplers G1 and G2, incident lights may be coupled to have a high optical coupling efficiency by using the grating couplers G1 and G2. A condition for coupling lights using the grating couplers G1 and G2 will be described with reference to FIG. 11 below.

Figure 11:
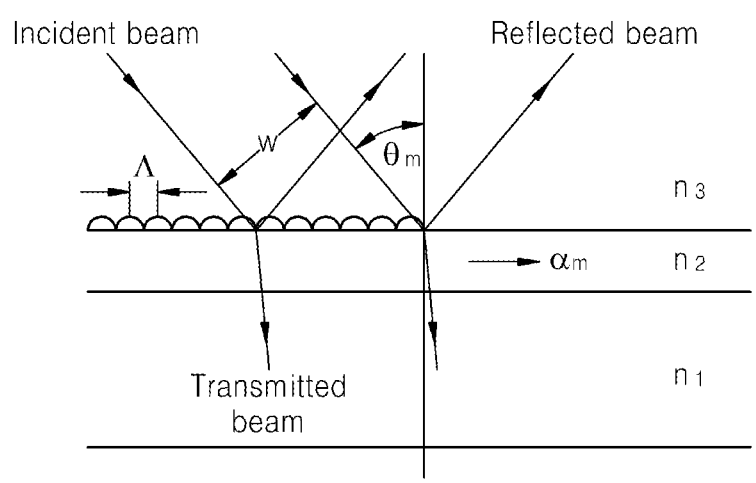
FIG. 11 is a diagram illustrating an optical coupling principle using a grating coupler, such as one shown in FIG. 10, according to an example embodiment of the inventive concepts.

FIG. 11 is a diagram illustrating an optical coupling principle using a grating coupler such as one shown in FIG. 10 according to an example embodiment of the inventive concepts.

Referring to FIG. 11, first, phases of incident beams should be identical so that the incident beams may be coupled to the grating couplers G1 and G2 with a high optical coupling efficiency. Such a phase matching condition may be expressed by Equation 2 below.

$$\beta v = \beta 0 + v2\pi/\Lambda,  \quad [\text{Equation 2}]$$

wherein 'v' denotes an integer, 'Λ' denotes an interval of gratings, 'βv' denotes a phase of a $v^{th}$ mode beam, and 'β0' denotes a phase of a fundamental mode beam.

A guiding condition for binding an incident beam within a waveguide may be expressed by Equation 3 below.

$$\alpha m = \kappa n3 \sin \theta m = 2\pi/\lambda 0 n3 \sin \theta m, \quad [\text{Equation 3}]$$

wherein 'm' denotes an integer, denotes a wavelength of a fundamental mode beam, and 'κ' denotes a wave that is a reciprocal of a wavelength. Also, 'αm' denotes a conditional value of a refractive index of an $m^{th}$ mode beam, and a 'θm' denotes an incident angle of the $m^{th}$ mode beam. In FIG. 11, 'w' denotes a width of an incident beam, 'n1' denotes a refractive index of a lower cladding layer, 'n2' denotes a refractive index of a core layer, and 'n3' denotes a refractive index of the outside of the waveguide or an upper cladding layer. To guide an incident beam along the waveguide, κn3<αm<κn2 should be satisfied.

Figure 12:
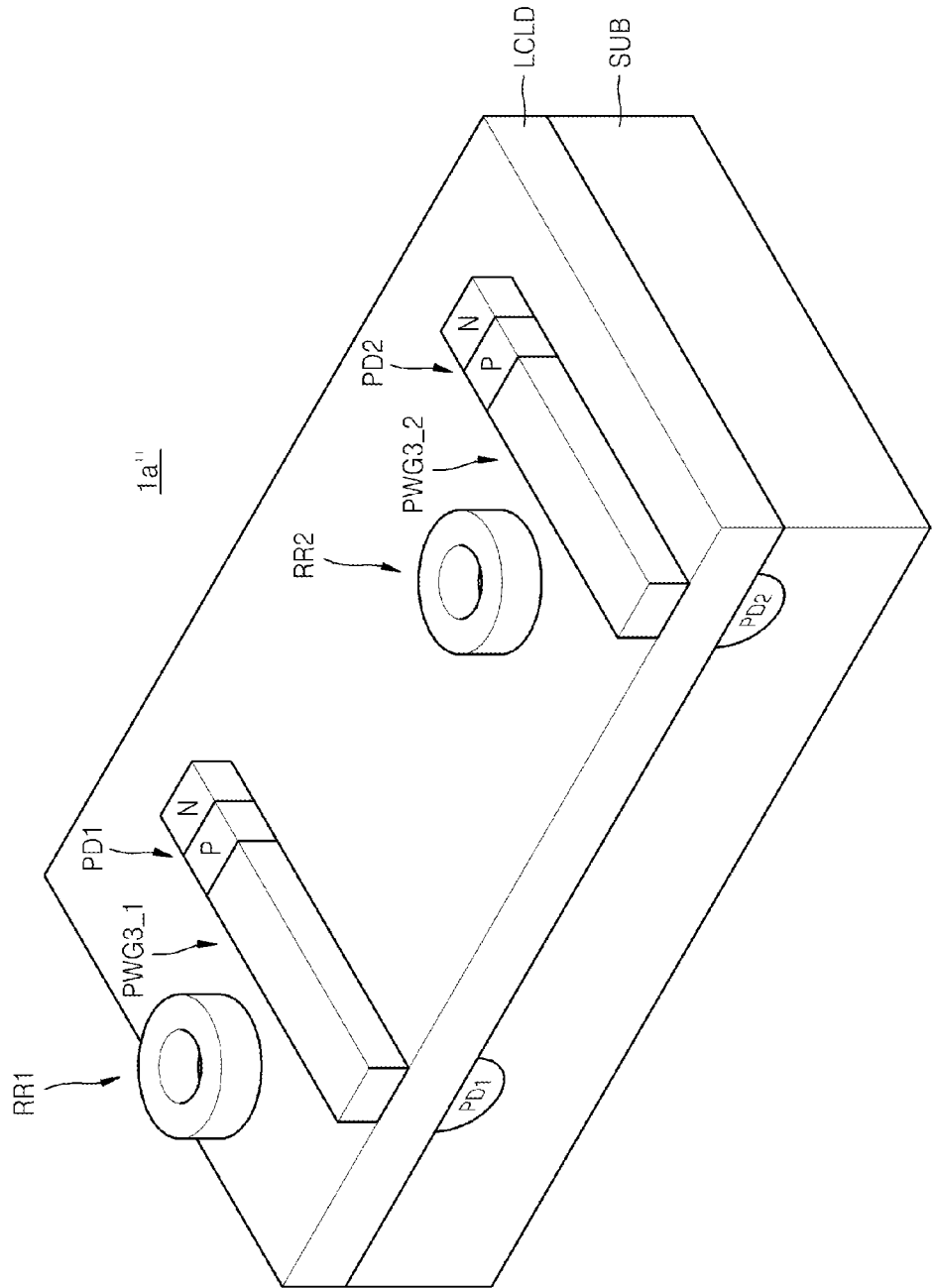
FIG. 12 is a perspective view of a part of an optical biosensor including the spectrometer of FIG. 7, according to another example embodiment of the inventive concepts.

FIG. 12 is a perspective view of a part of an optical biosensor 1a" including the spectrometer 30a' of FIG. 7, according to another example embodiment of the inventive concepts.

Referring to FIG. 12, in the optical biosensor 1a", a lower cladding layer LCLD may be disposed on a substrate SUB, and core layers of a plurality of ring oscillators RR1 and RR2 and core layers of a plurality of third optical waveguides PWG3_1 and PWG3_2 may be disposed on the lower cladding layer LCLD. For convenience of explanation, the core layers of the plurality of ring oscillators RR1 and RR2 will now be referred to as the plurality of ring oscillators RR1 and RR2, and the core layers of the plurality of third optical waveguides PWG3_1 and PWG3_2 will now be referred to as the plurality of third optical waveguides PWG3_1 and PWG3_2.

For convenience of explanation, the first and second optical waveguides PWG1 and PWG2 and the ring resonator RR0 included in the bio-sensing unit 20a of FIG. 3 are not illustrated in FIG. 12. According to an example embodiment of the inventive concepts, the second optical waveguide PWG2 may be disposed perpendicular to the plurality of third optical waveguides PWG3_1 and PWG3_2. However, the inventive concepts are not limited thereto and the second optical waveguide PWG2 and the plurality of third optical waveguides PWG3_1 and PWG3_2 may be arranged in other ways.

In the current embodiment, photo detectors PD1 and PD2 may be disposed at ends of the plurality of third optical waveguides PWG3_1 and PWG3_2, respectively. According to an example embodiment of the inventive concepts, the photo detectors PD1 and PD2 may be photodiodes according to a PN junction. According to another example embodiment of the inventive concepts, the photo detectors PD1 and PD2 may be Schottky diodes according to a metal-semiconductor junction. According to another example embodiment of the inventive concepts, the photo detectors PD1 and PD2 may be PIN photodiodes in which an I-layer is interposed between a P-layer and an N-layer. However, the inventive concepts are not limited thereto, and the photo detectors PD1 and PD2 may have other structures.

Figure 13:
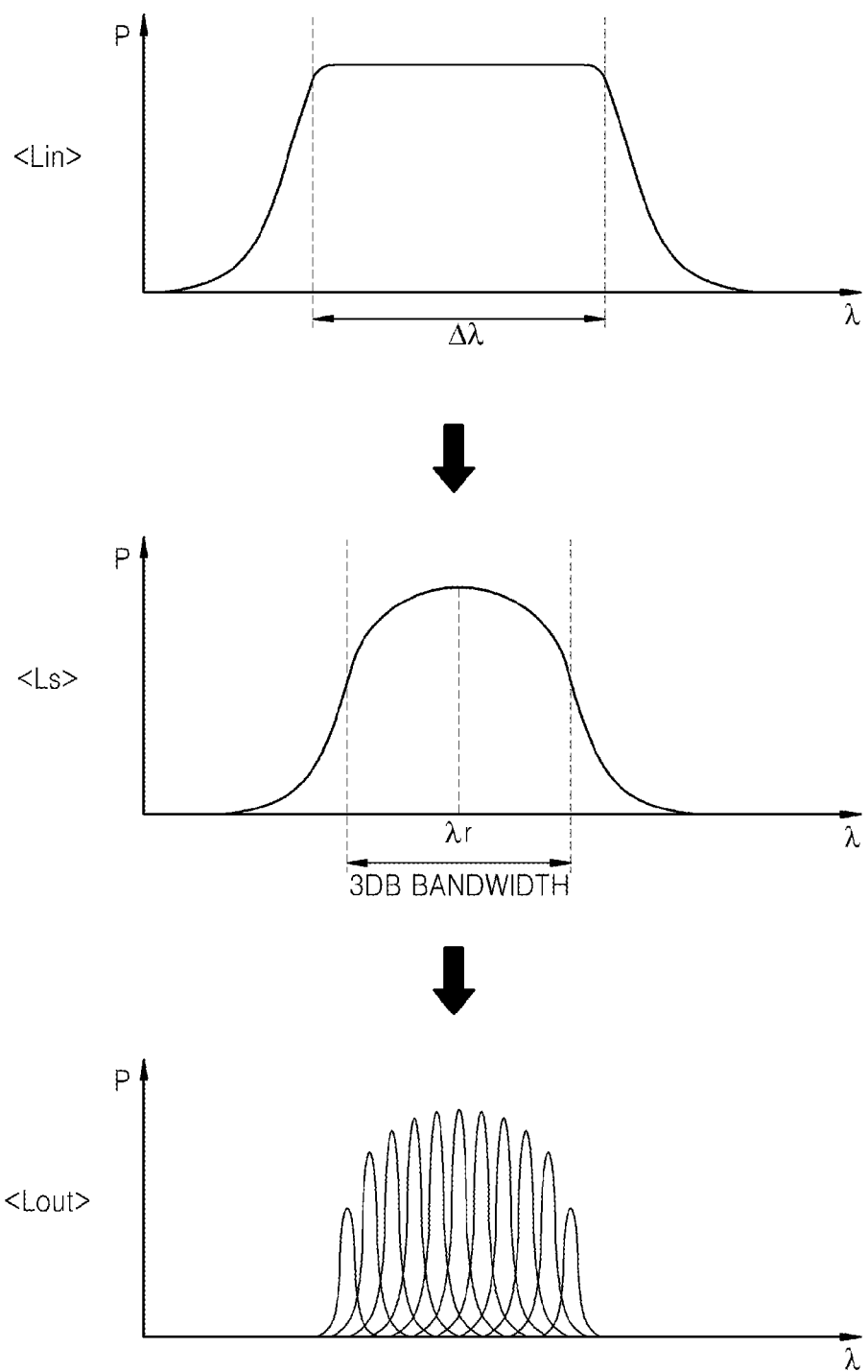
FIG. 13 is a graph illustrating spectrums of an input optical signal, a sensed optical signal, and a plurality of output optical signals generated by the optical biosensor of FIG. 2 according to an example embodiment of the inventive concepts.

FIG. 13 is a graph illustrating spectrums of an input optical signal Lin, a sensed optical signal Ls, and a plurality of output optical signals Lout1 to Lout11 generated by the optical biosensor 1a of FIG. 2 according to an example embodiment of the inventive concepts.

Referring to FIG. 13, the optical source 10a may generate an input optical signal Lin having a wavelength range Δλ and provide the input optical signal Lin to the first optical waveguide PWG1 of FIG. 3. For example, the wavelength range Δλ may be 10 nm, e.g., a range from 845 nm to 855 nm. According to another example embodiment of the inventive concepts, the input optical signal Lin may have a Gaussian waveform.

The bio-sensing unit 20a may generate a sensed optical signal Ls by extracting a resonant wavelength λr of the ring resonator RR0 from the input optical signal Lin, and provide the sensed optical signal Ls to the second optical waveguide PWG2 of FIG. 3. For example, 3 dB wavelengths of the sensed optical signal Ls may be 849.75 nm and 850.25 nm, and a 3 dB bandwidth of the sensed optical signal Ls may be 0.5 nm.

The spectrometer 30a may generate a plurality of output optical signals Lout by dividing the sensed optical signal Ls according to a wavelength. In detail, the spectrometer 30a may include N ring resonators that respectively generate N output optical signals having output wavelength components corresponding to N equal sub-bands divided from the 3 dB bandwidth of the sensed optical signal Ls. In this case, a waveform of the sensed optical signal Ls may be obtained by connecting peaks of the plurality of output optical signals Lout.

Figure 14:
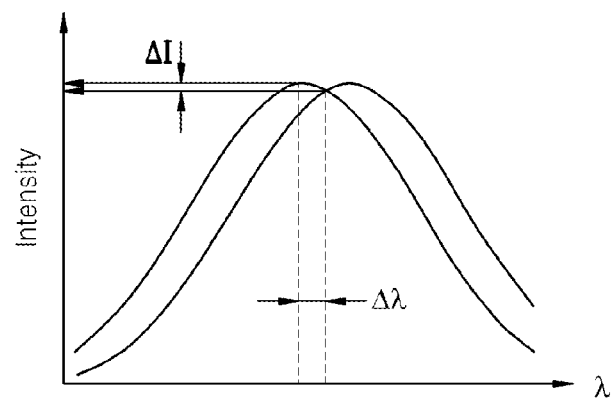
FIG. 14 is a graph illustrating a variation in the intensity of an output optical signal according to a wavelength thereof, generated in the optical biosensor of FIG. 2 according to an example embodiment of the inventive concepts.

FIG. 14 is a graph illustrating a variation in the intensity of an output optical signal according to a wavelength thereof, generated in the optical biosensor 1a of FIG. 2 according to an example embodiment of the inventive concepts.

Referring to FIG. 14, a resonant wavelength λr of the ring resonator RR0 included in the bio-sensing unit 20a may be changed by Δλ due to interactions of biomaterials, i.e., combining a probe material and a target material. Thus, the wavelength of the sensed optical signal Ls may be changed by Δλ, and the wavelength of the output optical signal Lout may also be changed by Δλ. Thus, a variation in the resonant wavelength λr may be measured using a change in an optical intensity detected by the detecting unit 40a, and the concentrations of the biomaterials may be determined using the variation in the resonant wavelength λr.

Figure 15:
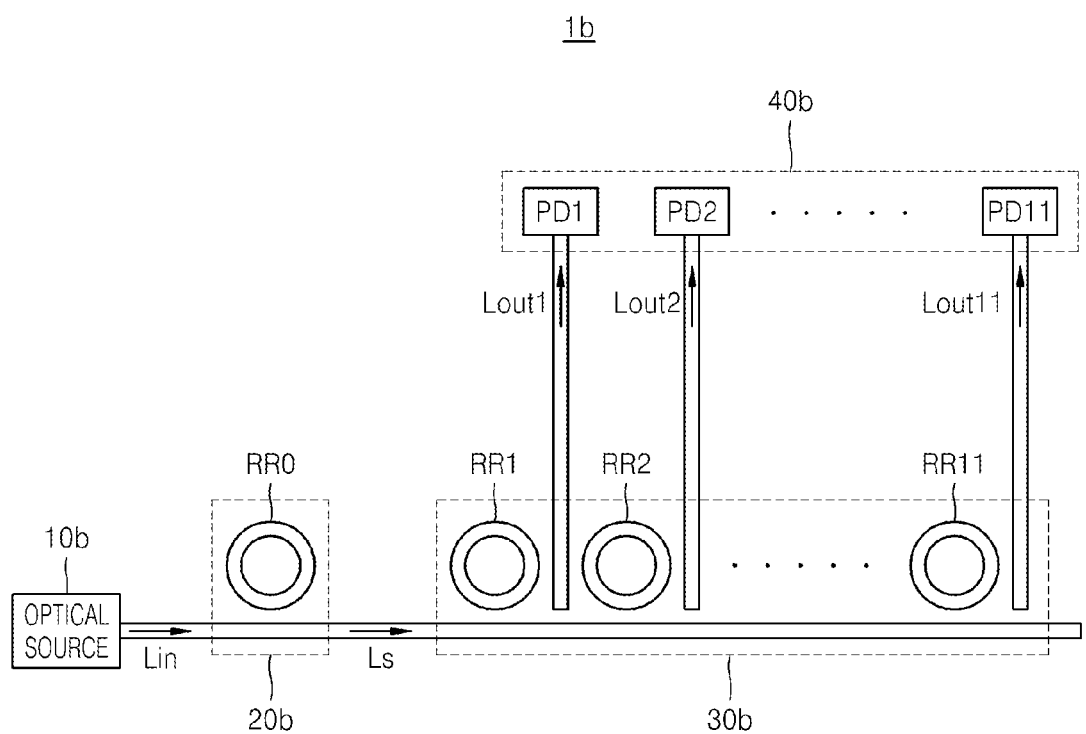
FIG. 15 illustrates another example of the optical biosensor of FIG. 1.

FIG. 15 illustrates an optical biosensor 1b that is another example of the optical biosensor of FIG. 1.

Referring to FIG. 15, the optical biosensor 1b may include an optical source 10b, a bio-sensing unit 20b, a spectrometer 30b, and a detecting unit 40b. The optical biosensor 1b according to the current embodiment is a modified example of the optical biosensor 1a of FIG. 2.

The optical source 10b may generate an input optical signal Lin and provide the input optical signal Lin to the bio-sensing unit 20b. Specifically, the input optical signal Lin may include a wavelength component having a desired (or, alternatively a predetermined) range, e.g., a wavelength component ranging from several tens of nanometers to several hundreds of nanometers. For example, 3 dB wavelengths of the input optical signal Lin may be 845 nm and 855 nm. In this case, a 3 dB bandwidth or FWHM of the input optical signal Lin may be 10 nm. However, the inventive concepts are not limited thereto, and the input optical signal Lin and a waveform and wavelength range of the input optical signal Lin may be set to other values.

The bio-sensing unit 20b may generate a sensed optical signal Ls, the wavelength of which varies according to whether a biomaterial exists or the concentration of the biomaterial, from the input optical signal Lin. In detail, the sensed optical signal Ls may be an optical signal obtained by dissipating a resonant wavelength corresponding to the concentration of the biomaterial from a wavelength component of the input optical signal Lin. In the current embodiment, the bio-sensing unit 20b may include a ring resonator RR0 for dissipating the resonant wavelength from the input optical signal Lin. A structure of the bio-sensing unit 20b will be described in detail with reference to FIG. 16 below.

The spectrometer 30b may include a plurality of ring oscillators RR1 to RR11. The plurality of ring oscillators RR1 to RR11 may generate a plurality of output optical signals Lout1 to Lout11 by dividing the sensed optical signal Ls according to a wavelength, respectively. In the current embodiment, eleven ring oscillators RR1 to RR11 are included in the spectrometer 30b, but the number of ring resonators that may be included in the spectrometer 30b may vary according to embodiments of the inventive concepts.

The detecting unit 40b may include a plurality of photo detectors PD1 to PD11. The plurality of photo detectors PD1 to PD11 may transform the plurality of output optical signals Lout1 to Lout11 into electrical signals Sout1 to Sout11, respectively. The plurality of photo detectors PD1 to PD11 may be connected to the plurality of ring oscillators RR1 to RR11, respectively. The number of photo detectors PD1 to PD11 may correspond to that of ring oscillators RR1 to RR1. For example, the plurality of photo detectors PD1 to PD11 may include a photodiode, a phototransistor, a CCD image sensor, a CMOS image sensor, a TOF sensor, etc.

Figure 16:
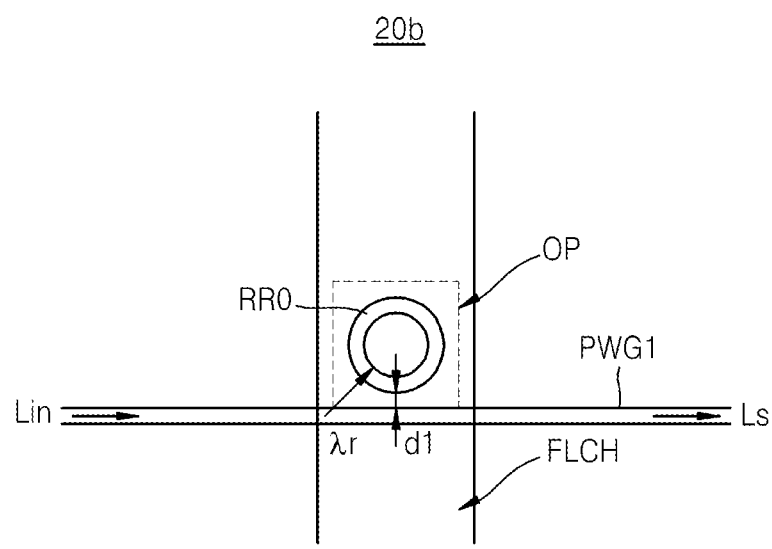
FIG. 16 specifically illustrates a bio-sensing unit of FIG. 15.

FIG. 16 specifically illustrates the bio-sensing unit 20b of FIG. 15.

Referring to FIG. 16, the bio-sensing unit 20b may include a first waveguide PWG1 and a ring resonator RR0. A fluidic channel FLCH may be disposed above the first optical waveguide PWG1 and the ring resonator RR0. An opening OP via which the ring resonator RR0 may be exposed to the fluidic channel FLCH may be disposed above the ring resonator RR0. In this case, the first optical waveguide PWG1 may be a straight line type optical waveguide, and the ring resonator RR0 may be an optical waveguide having a circular or race track shape.

The ring resonator RR0 may be spaced from the first optical waveguide PWG1 by a first interval d1. According to an example embodiment of the inventive concepts, the ring resonator RR0 may be horizontally spaced from the first optical waveguide PWG1 by the first interval d1. According to another example embodiment of the inventive concepts, the ring resonator RR0 may be vertically spaced from the first optical waveguide PWG1 by the first interval d1.

A wavelength that satisfies a resonating condition of the ring resonator RR0, i.e., a resonant wavelength $\lambda r$, is transferred to the ring resonator RR0 and thus dissipates from a wavelength of the input optical signal Lin that is supplied from the optical source 10b of FIG. 15 and is totally reflected to travel within the first optical waveguide PWG1 due to total reflection. An optical signal obtained by dissipating the resonant wavelength $\lambda r$ from the wavelength of the input optical signal Lin continuously travels within the first optical waveguide PWG1 and is then output as a sensed optical signal Ls.

Thus, the sensed optical signal Ls generated by the bio-sensing unit 20b is an optical signal obtained by dissipating the resonant wavelength $\lambda r$ from the input optical signal Lin. The resonant wavelength $\lambda r$ may vary according to the concentration of a biomaterial sensed by the bio-sensing unit 20b. Thus, a wavelength component of the sensed optical signal Ls may vary according to the concentration of the biomaterial.

Figure 17:
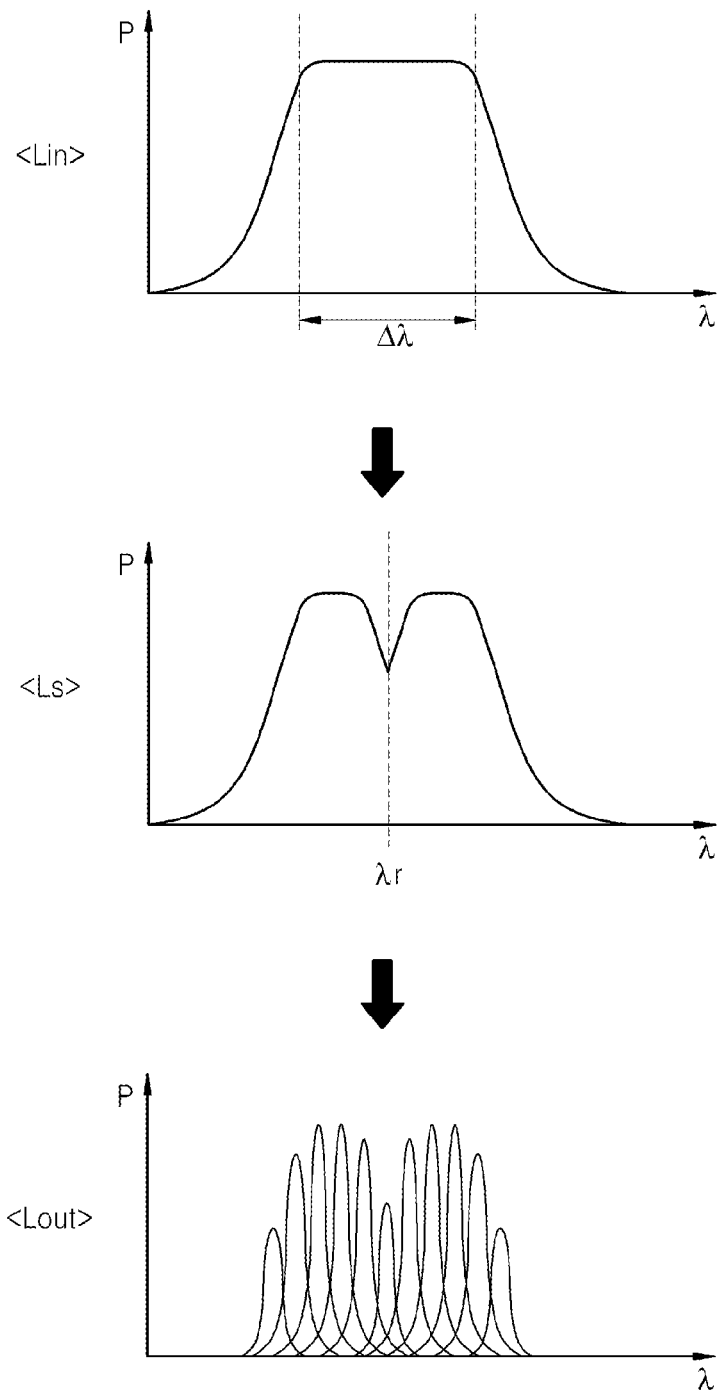
FIG. 17 is a graph illustrating spectrums of an input optical signal, a sensed optical signal, and a plurality of output optical signals generated by the optical biosensor of FIG. 15 according to another example embodiment of the inventive concept.

FIG. 17 is a graph illustrating spectrums of an input optical signal Lin, a sensed optical signal Ls, and a plurality of output optical signals Lout1 to Lout11 generated by the optical biosensor 1b of FIG. 15 according to another example embodiment of the inventive concepts.

Referring to FIG. 17, the optical source 10b generates an input optical signal Lin having a wavelength range $\Delta\lambda$, and provides the input optical signal Lin to the first optical waveguide PWG1. For example, the wavelength range $\Delta\lambda$ may be 10 nm, e.g., a range from 845 nm to 855 nm. According to another example embodiment of the inventive concepts, the input optical signal Lin may have a Gaussian waveform.

The bio-sensing unit 20b may generate a sensed optical signal Ls obtained by dissipating the resonant wavelength $\lambda r$ of the ring resonator RR0 from the input optical signal Lin. The sensed optical signal Ls may continuously travel within the first optical waveguide PWG1.

The spectrometer 30b may generate a plurality of output optical signals Lout by dividing the sensed optical signal Ls according to a wavelength. Specifically, the spectrometer 30b may include N ring resonators that generate N output optical signals having output wavelength components corresponding to N equal sub-bands divided from a wavelength range of the sensed optical signal Ls, respectively. In this case, a waveform of the sensed optical signal Ls may be obtained by connecting peaks of the plurality of output optical signals Lout.

Figure 18:
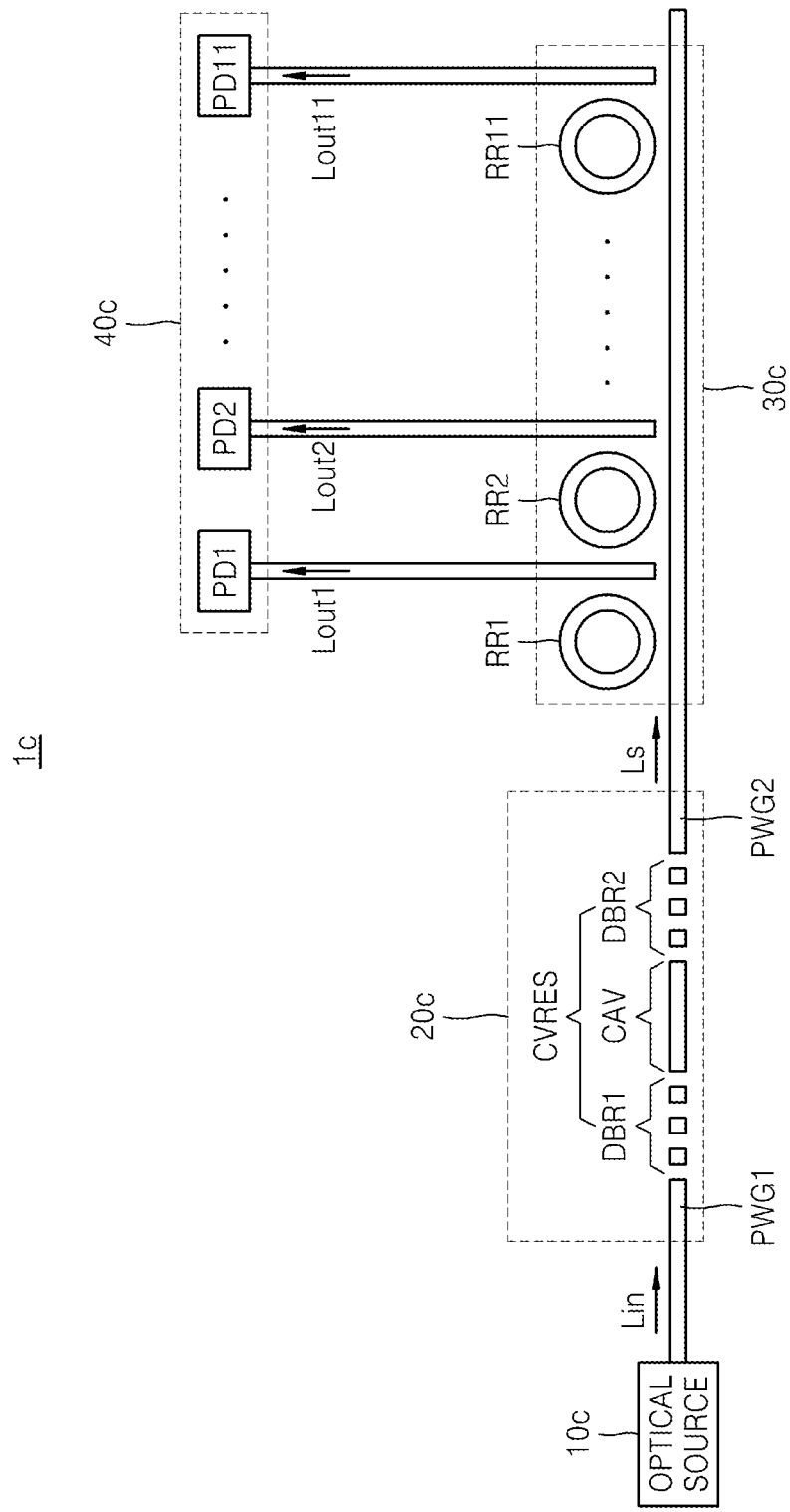
FIG. 18 illustrates another example of the optical biosensor of FIG. 1.

FIG. 18 illustrates an optical biosensor 1c that is another example of the optical biosensor of FIG. 1.

Referring to FIG. 18, the optical biosensor 1c may include an optical source 10c, a bio-sensing unit 20c, a spectrometer 30c, and a detecting unit 40c. The optical biosensor 1c according to the current embodiment is a modified example of the optical biosensor 1a of FIG. 2.

The optical source 10c may generate an input optical signal Lin and provide the input optical signal Lin to the bio-sensing unit 20c. In detail, the input optical signal Lin may include a wavelength component having a desired (or, alternatively a predetermined) range, e.g., a wavelength component ranging from several tens of nanometers to several hundreds of nanometers. For example, 3 dB wavelengths of the input optical signal Lin may be 845 nm and 855 nm, and a 3 dB bandwidth or FWHM of the input optical signal Lin may be 10 nm. However, the inventive concepts are not limited thereto, and a waveform and wavelength range of the input optical signal Lin may be set to other values.

The bio-sensing unit 20c may generate a sensed optical signal Ls, the wavelength of which varies according to whether a biomaterial exists or the concentration of the biomaterial, from the input optical signal Lin. Specifically, the sensed optical signal Ls may be an optical signal obtained by extracting a resonant wavelength corresponding to the concentration of the biomaterial from a wavelength component of the input optical signal Lin.

In the current embodiment, the bio-sensing unit 20c may include a first optical waveguide PWG1, a cavity resonator CVRES, and a second optical waveguide PWG2. In this case, the cavity resonator CVRES may extract only the resonant wavelength from a wavelength of the input optical signal Lin and provide extracted signal as the sensed optical signal Ls to the second optical waveguide PWG2.

The cavity resonator CVRES may include two distributed bragg reflectors Distributed Bragg Reflectors DBR1 and DBR2, and a cavity CAV. The distributed bragg reflectors DBR1 and DBR2 reflect a particular wavelength of a wavelength of the input optical signal Lin. Thus, the two distributed bragg reflectors DBR1 and DBR2 and the cavity CAV may be combined to function as a resonator. Thus, only a resonant wavelength that satisfies resonating conditions may be generated as the sensed optical signal Ls and then be output to the second optical waveguide PWG2.

Although not shown, an opening may be formed above the cavity CAV. Thus, when receptors corresponding to a biomaterial that is to be sensed are attached to an upper portion of the cavity CAV and the receptors are combined with the biomaterial, an effective refractive index of the cavity resonator CVRES may vary according to the degree of combining (i.e., the concentration of the biomaterial). Accordingly, the resonant wavelength varies according to the concentration of the biomaterial, thereby changing a wavelength component of the sensed optical signal Ls.

The spectrometer 30c may include a plurality of ring oscillators RR1 to RR11. The plurality of ring oscillators RR1 to RR11 may generate a plurality of output optical signals Lout1 to Lout11 by dividing the sensed optical signal Ls according to a wavelength, respectively. In the current embodiment, eleven ring oscillators RR1 to RR11 are included in the spectrometer 30c, but the number of ring resonators that may be included in the spectrometer 30c may vary according to various embodiments of the inventive concepts.

The detecting unit 40c may include a plurality of photo detectors PD1 to PD 11. The plurality of photo detectors PD1 to PD11 may transform the plurality of output optical signals Lout11 to Lout11 into electrical signals Sout1 to Sout11, respectively. In this case, the plurality of photo detectors PD1 to PD11 may be connected to the plurality of ring oscillators RR1 to RR11, respectively. The number of photo detectors PD1 to PD11 may correspond to the number of ring oscillators RR1 to RR1. For example, the plurality of photo detectors PD1 to PD11 may include a photodiode, a phototransistor, a CCD image sensor, a CMOS image sensor, a TOF sensor, etc.

Figure 19:
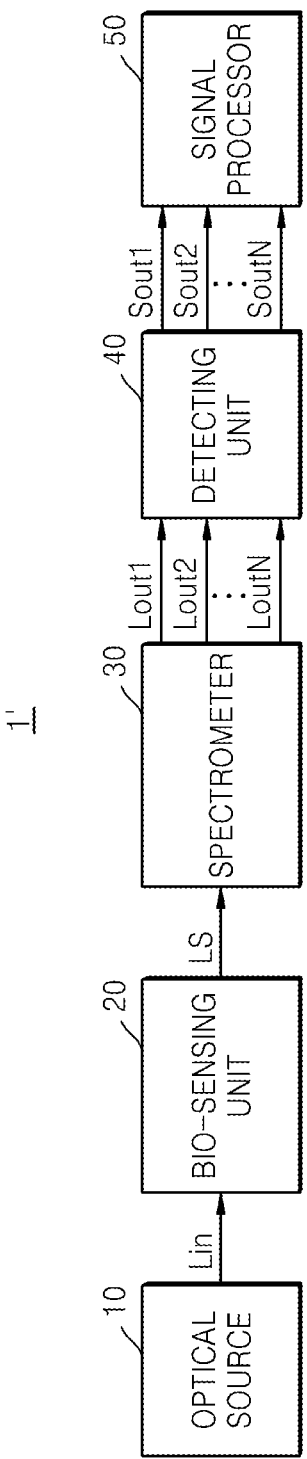
FIG. 19 is a block diagram of an optical biosensor according to another example embodiment of the inventive concept.

FIG. 19 is a block diagram of an optical biosensor 1' according to another example embodiment of the inventive concepts.

Referring to FIG. 19, the optical biosensor 1' may include an optical source 10, a bio-sensing unit 20, a spectrometer 30, a detecting unit 40, and a signal processor 50. The optical biosensor 1' according to the current embodiment is a modified example of the optical biosensor 1 of FIG. 1. Some elements of the optical biosensor 1' according to the current embodiment are the same as elements of the optical biosensor 1 of FIG. 1. The same elements are denoted by the same reference numeral, and the elements of the optical biosensor 1' according to the current embodiment that are the same as those of the optical biosensor 1 of FIG. 1 are not described again here. The optical biosensor 1' according to the current embodiment will now be described by focusing on the difference between the optical biosensor 1' and the optical biosensor 1 of FIG. 1.

The signal processor 50 determines the concentration of a biomaterial by receiving electrical signals Sout1 to SoutN output from the detecting unit 40. The signal processor 50 may have stored data regarding electrical signals according to the concentrations of biomaterials, and determine the concentration of a sensed biomaterial based on the stored data when the concentration of the biomaterial is measured. Otherwise, the concentration of a biomaterial may be calculated and determined, based on the features of a resonator included in the bio-sensing unit 20 and a change in electrical signals Sout1 to SoutN before and after receptors and the biomaterial are combined. In addition, the concentration of the biomaterial may be determined in other ways, based on the electrical signals Sout 1 to SoutN.

Figure 20:
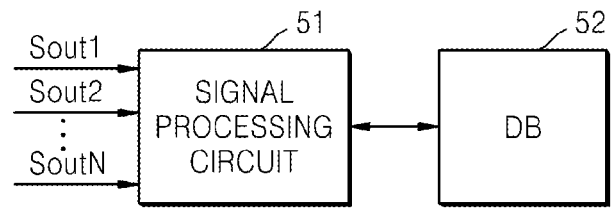
FIG. 20 is a detailed block diagram of a signal processor illustrated in FIG. 19 according to an example embodiment of the inventive concepts.

FIG. 20 is a detailed block diagram of the signal processor 50 illustrated in FIG. 19 according to an example embodiment of the inventive concepts.

Referring to FIG. 20, the signal processor 50 may include a signal processing circuit 51 and a database 52.

The signal processing circuit 51 determines the concentration of a biomaterial based on input electrical signals Sout1 to SoutN. The database 52 is a block that stores data regarding electrical signals according to the concentrations of biomaterials. In the database 52, data regarding various biomaterials may be stored.

For example, when the electrical signals Sout1 to SoutN are input to the signal processing circuit 51, the signal processing circuit 51 transmits information regarding the type of the biomaterial and the data regarding the electrical signals Sout1 to SoutN to the database 52, and requests the database 52 to provide the concentration of the biomaterial. Otherwise, the signal processing circuit 51 may request the database 52 to provide data regarding a particular biomaterial, and determine the concentration of the biomaterial based on the data transmitted from the database 52 and the data regarding the input electrical signals Sout1 to SoutN.

FIGS. 21 to 24 are cross-sectional views sequentially illustrating a method of manufacturing an optical biosensor, according to an example embodiment of the inventive concepts.

Figure 21:
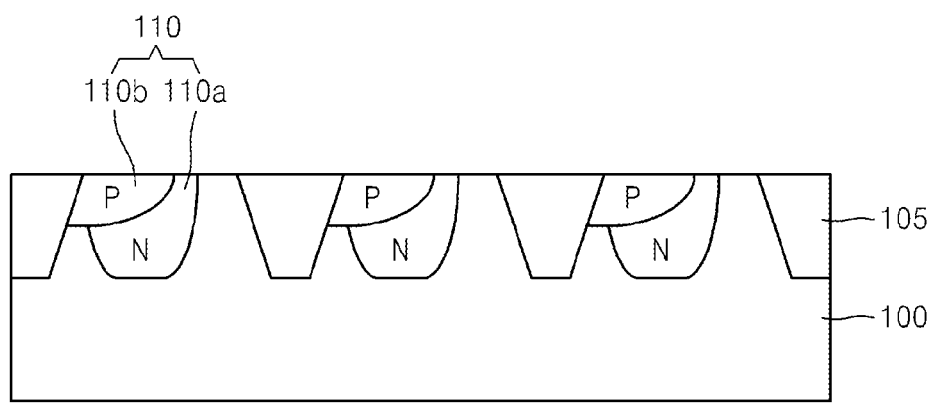
FIGS. 21 to 24 are cross-sectional views sequentially illustrating a method of manufacturing an optical biosensor, according to an example embodiment of the inventive concepts.

Referring to FIG. 21, a substrate 100 is provided. The substrate 100 may be divided into a pixel array area (not shown) and a peripheral circuit area. In the pixel array area, a plurality of unit pixels each including a photodiode region (not shown) and a transistor region (not shown) are disposed. A photodiode, which is a light-receiving unit, is formed in the photodiode region, and transistors, e.g., a transfer transistor, a reset transistor, a driving transistor, and a select transistor, are formed in the transistor region. In the peripheral circuit area, a driving transistor for driving the transistors included in the pixel array area is disposed. In FIGS. 21 to 24, only a part of the photodiode region is illustrated for convenience of explanation.

The substrate 100 may be a semiconductor substrate. For example, the semiconductor substrate may include one of silicon, a silicon-on-insulator, silicon-on-sapphire, germanium, silicon-germanium, and gallium-arsenide. In the current embodiment, the substrate 100 may be a P-type semiconductor substrate. In the substrate 100, an isolation film 105 that defines an active area is formed. The isolation film 105 may be formed, for example, according to a shallow trench isolation (STI) process.

A photodiode 110 having a PN junction diode shape is obtained by forming a first well 110a by implanting N-type impurities, e.g. phosphor (P), arsenic (As), or antimony (Sb), into the photodiode region of the substrate 100 and by forming a second well 110b by implanting P-type impurities, e.g., boron (B), gallium (Ga), and indium (In), into the photodiode region. However, the inventive concepts are not limited thereto, and the first well 110a may be formed by implanting P-type impurities, and the second well 110b may be formed by implanting N-type impurities. Also, the order in which the first well 110 and the second well 110 are formed may be changed.

Figure 22:
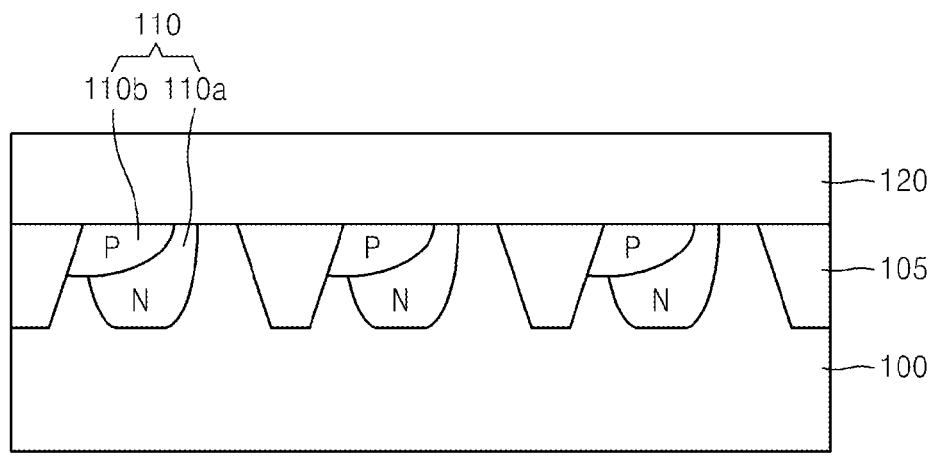

Referring to FIG. 22, an insulating layer 120 is formed on the substrate 100 in which the photodiode 110 is formed. For example, the insulating layer 120 may be an oxide layer. In this case, the insulating layer 120 may correspond to a lower cladding layer.

Figure 23:
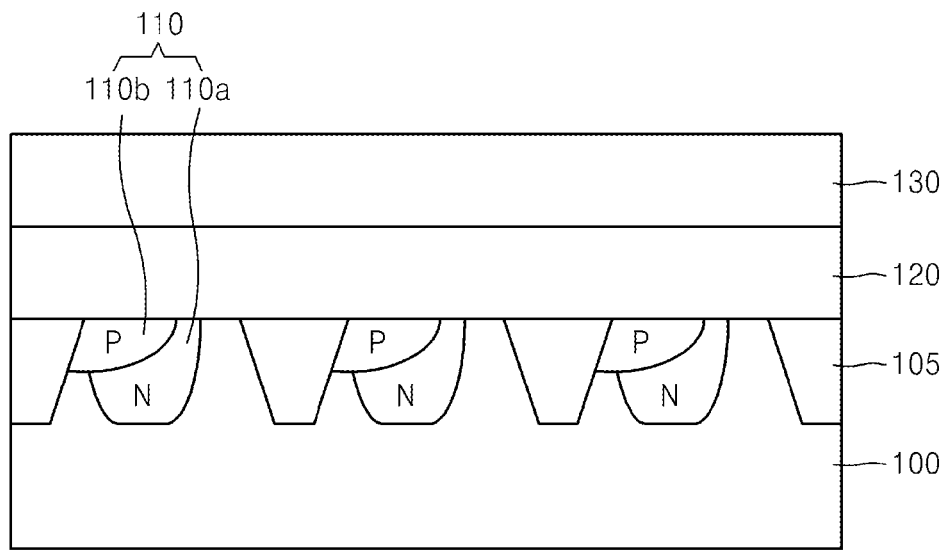

Referring to FIG. 23, a core layer 130 is formed on the insulating layer 120. For example, the core layer 130 may be a silicon layer or a silicon nitride layer. In this case, a material used to form the core layer 130 should be selected such that a refractive index of the core layer 130 is greater than that of the insulating layer 120.

Figure 24:
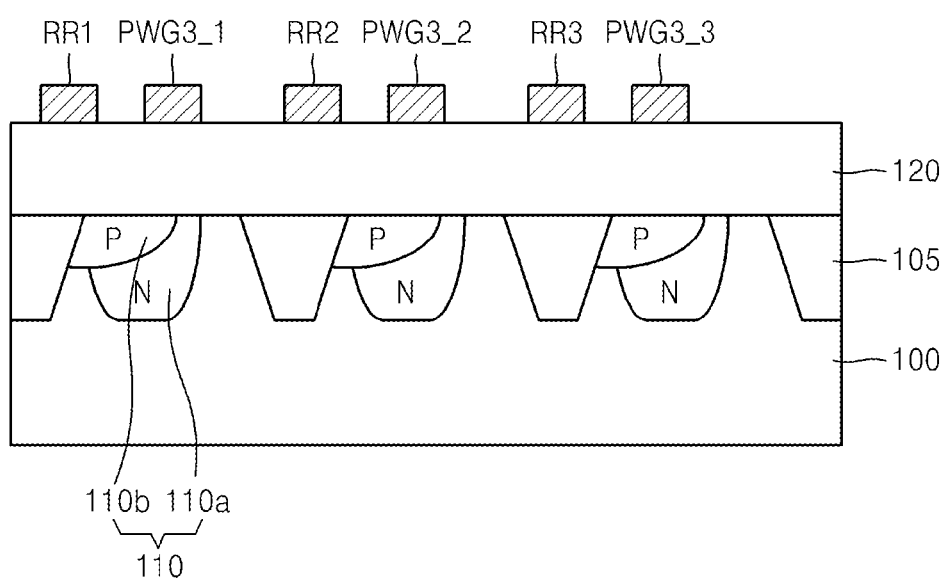

Referring to FIG. 24, the core layer 130 is patterned to obtain a plurality of ring oscillators RR1 to RR3 and a plurality of third optical waveguides PWG3_1 to PWG3_3. Although not shown, the core layer 130 may be patterned to obtain the ring resonator RR0 and the first and second optical waveguides PWG1 and PWG2 included in the bio-sensing unit 20 of FIG. 3. Specifically, the plurality of ring oscillators RR1 to RR3 and the plurality of third optical waveguides PWG3_1 to PWG3_3 are formed by applying a photoresist on the core layer 130, irradiating, for example, ultraviolet (UV) light onto the photoresist by using a photo mask (not shown), and performing an etch process on the resultant structure.

Although not shown, grating couplers may be formed at ends of the first to third optical waveguides PWG1, PWG2, and PWG3_1 to PWG3_11. The grating couplers may be connected to optical fiber so as to transmit/receive an optical signal.

According to another example embodiment of the inventive concepts, each of a plurality of detectors may be formed on one end of one of the third optical waveguides PWG3_1 to PWG3_11. For example, the plurality of detectors may include at least one of a photodiode, a phototransistor, a TOF sensor, a CMOS sensor, and a CCD sensor.

Figure 25:
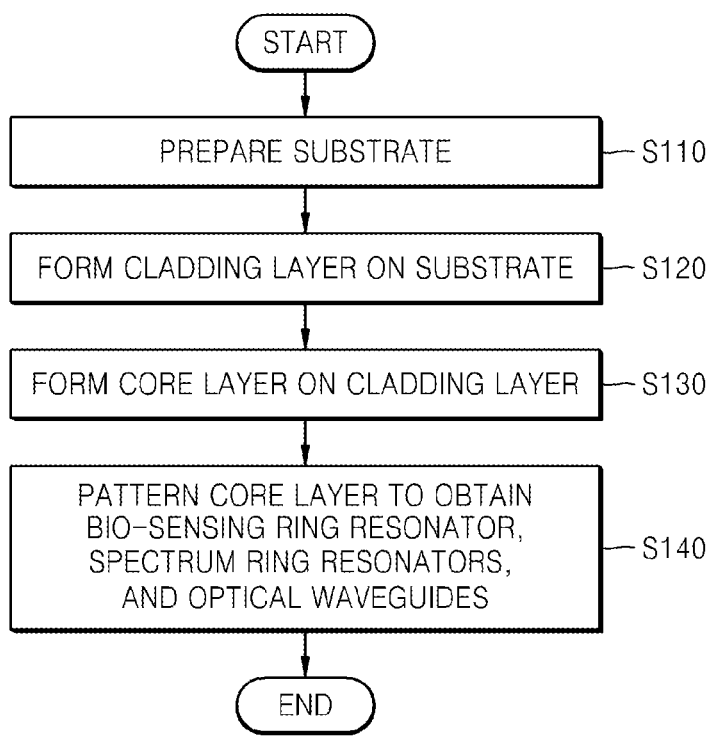
FIG. 25 is a flowchart illustrating a method of manufacturing an optical biosensor, according to an example embodiment of the inventive concepts.

FIG. 25 is a flowchart illustrating a method of manufacturing an optical biosensor, according to an example embodiment of the inventive concepts. The method of FIG. 25 according to the current embodiment may be used to manufacture the optical biosensors 1 and 1' illustrated in FIGS. 1 to 24. Thus, the descriptions about the optical biosensors 1 and 1' illustrated in FIGS. 1 to 24 may also be applied to the method of FIG. 25.

In operation S110, a substrate is provided. In the current embodiment, the substrate may be a semiconductor substrate.

In operation S120, a cladding layer is formed on the substrate on which a detecting device is formed. In the current embodiment, the cladding layer may include a material, the refractive index of which is less than that of a core layer. For example, the cladding layer may be an oxide layer.

In operation S130, the core layer is formed on the cladding layer. For example, the core layer may be a silicon layer or a silicon nitride layer.

In operation S140, the core layer is patterned to obtain a bio-sensing ring resonator, a plurality of spectrum ring resonators, and a plurality of optical waveguides. Specifically, the plurality of optical waveguides may include a first optical waveguide that receives an input optical signal and provides the input optical signal to the bio-sensing ring resonator, a second optical waveguide that receives a sensed optical signal from the bio-sensing ring resonator and provides the sensed optical signal to the plurality of spectrum ring resonators, and a plurality of third optical waveguides that receive a plurality of output optical signals from the plurality of spectrum ring resonators, respectively.

According to another example embodiment of the inventive concepts, the method of FIG. 25 may further include forming a plurality of detectors on the substrate before the cladding layer is formed. According to another example embodiment of the inventive concepts, the method of FIG. 25 may further include forming each of a plurality of detectors on one end of one of the plurality of third optical waveguides. According to another example embodiment of the inventive concepts, the method of FIG. 25 may further include forming each of a plurality of grating couplers on one end of one of the plurality of third optical waveguides.

Figure 26:
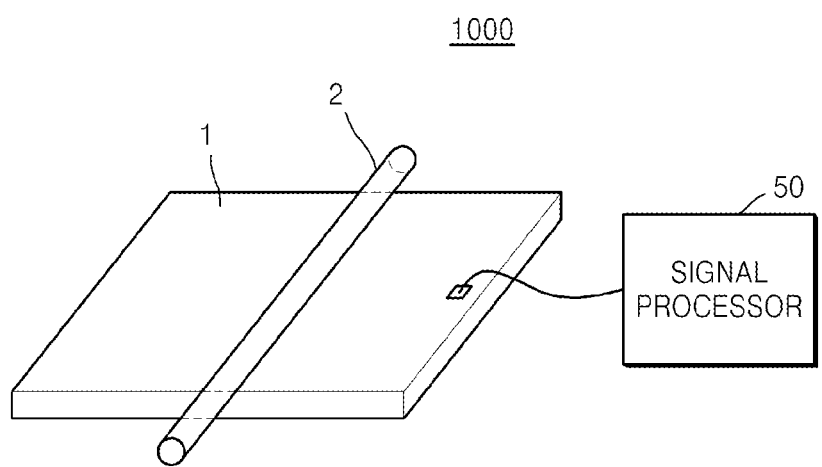
FIG. 26 is a diagram of a bio-sensing system according to an example embodiment of the inventive concepts.

FIG. 26 is a diagram of a bio-sensing system 1000 according to an example embodiment of the inventive concepts.

Referring to FIG. 26, the bio-sensing system 1000 may include a biosensor chip 1, a fluidic channel 2, and a signal processor 50.

The biosensor chip 1 senses the concentration of a biomaterial based on optical characteristics and outputs a result of the sensing as an electrical signal. According to the current embodiment, the biosensor chip 1 may be the same as the optical biosensor 1 of FIG. 1. Thus, since the biosensor chip 1 is capable of sensing the concentration of the biomaterial by generating an optical signal and outputting a result of the sensing as an electrical signal, an additional optical source, a spectrometer system, or the like is not required. Accordingly, the bio-sensing system 1000 may be manufactured to be compact, consume low power, and be portable.

The fluidic channel 2 is a path in which a biomaterial flows. The fluidic channel 2 is arranged on the biosensor chip 1, and particularly, a location where an opening of the bio-sensing unit 20 is formed. When a fluid or gas containing the biomaterial flows via the fluidic channel 2, the biomaterial may contact the biosensor chip 1 via the opening. The fluidic channel 2 may be a micro fluidic channel or may be a fluidic channel formed on a micro fluidic chip. Although FIG. 26 illustrates the fluidic channel 2 in the form of a straight line, the fluidic channel 2 may have other shapes.

The signal processor 50 determines the concentration of the biomaterial based on electrical signals output from the biosensor chip 1. The signal processor 50 may be located in a processing system, e.g., a computer, to receive the electrical signal output from the biosensor chip 1 via a connecting terminal or a connecting line. Otherwise, the signal processor 50 may be installed in an independent biosensor system, together with the biosensor chip 1 and the fluidic channel 2.

While the inventive concepts has been particularly shown and described with reference to Example embodiments thereof, it will be understood that various changes in form and details may be made therein without departing from the spirit and scope of the following claims.

What is claimed is:

1. An optical biosensor comprising:
   a bio-sensing unit including a first ring resonator configured to sense a biomaterial by receiving an input optical signal and generating a sensed optical signal having a wavelength which varies according to the biomaterial; and
   a spectrometer configured to generate a plurality of output optical signals by passing the sensed optical signal through a plurality of second ring resonators optically coupled to the first ring resonator, the plurality of second ring resonators having different resonant wavelengths, the plurality of output optical signals having intensities that vary based on the biomaterial.

2. The optical biosensor of claim 1, wherein the sensed optical signal is a signal obtained by one of extracting a resonant wavelength from a wavelength component of the input optical signal and dissipating the resonant wavelength from the input optical signal, the resonant wavelength varying according to a concentration of the biomaterial.

3. The optical biosensor of claim 2, wherein the first ring resonator is configured to extract the resonant wavelength from the wavelength component of the input optical signal.

4. The optical biosensor of claim 2, wherein the bio-sensing unit comprises;
  a first optical waveguide configured to receive the input optical signal;
  the first ring resonator configured to extract the resonant wavelength from the wavelength component of the input optical signal, the resonant wavelength extracted via an interval between the first ring resonator and the first optical waveguide; and
  a second optical waveguide configured to provide the resonant wavelength to the spectrometer as the sensed optical signal via an interval between the second optical waveguide and the first ring resonator.

5. The optical biosensor of claim 2, wherein the bio-sensing unit comprises:
  an optical waveguide configured to receive the input optical signal; and
  the first ring resonator configured to,
    generate the sensed optical signal by dissipating the resonant wavelength from a wavelength of the input optical signal via an interval between the first ring resonator and the optical waveguide, and
    provide the sensed optical signal to the optical waveguide.

6. The optical biosensor of claim 2, wherein the bio-sensing unit comprises:
  a first optical waveguide configured to receive the input optical signal;
  the resonator the first ring resonator being a cavity resonator configured to extract the resonant wavelength from a wavelength of the input optical signal and provide the resonant wavelength as the sensed optical signal; and
  a second optical waveguide configured to receive the sensed optical signal and provide the sensed optical signal to the spectrometer.

7. The optical biosensor of claim 1, wherein the spectrometer comprises:
  a first optical waveguide configured to receive the sensed optical signal;
  the plurality of second ring resonators configured to extract a plurality of resonant wavelengths from the wavelength of the sensed optical signal via intervals between the plurality of second ring resonators and the first optical waveguide; and
  a plurality of second optical waveguides configured to, receive the plurality of resonant wavelengths via intervals between the plurality of second optical waveguides and the plurality of second ring resonators, and provide the plurality of resonant wavelengths as the plurality of output optical signals.

8. The optical biosensor of claim 7, wherein the plurality of second ring resonators extract different resonant wavelengths, respectively.

9. The optical biosensor of claim 7, further comprising:
  grating couplers located at ends of the plurality of second optical waveguides.

10. The optical biosensor of claim 1, wherein the spectrometer comprises:
  N second ring resonators configured to generate N output optical signals having output wavelength components corresponding to N equal sub-bands divided from a 3 dB bandwidth of the sensed optical signal, respectively.

11. The optical biosensor of claim 1, wherein the bio-sensing unit and the spectrometer are on a same semiconductor substrate.

12. The optical biosensor of claim 1, further comprising:
  a detecting unit configured to transform the plurality of output optical signals into electrical signals.

13. The optical biosensor of claim 12, wherein the detecting unit comprises:
  a plurality of detectors configured to receive the plurality of output optical signals, respectively.

14. The optical biosensor of claim 13, wherein the plurality of detectors comprise:
  at least one of a photodiode,
  a phototransistor,
  a time-of-flight (TOF) sensor,
  a complementary metal-oxide semiconductor (CMOS) sensor,
  and a charge-coupled device (CCD) sensor.

15. The optical biosensor of claim 12, wherein the bio-sensing unit, the spectrometer, and the detecting unit are formed or packaged on the same semiconductor substrate.

16. The optical biosensor of claim 12, further comprising:
  a signal processor configured to determine a concentration of the biomaterial based on the electrical signals output from the detecting unit.

17. The optical biosensor of claim 1, further comprising:
  an optical source configured to provide the input optical signal to the bio-sensing unit.

18. An optical biosensor comprising:
  a bio-sensing ring resonator configured to extract a sensed optical signal from an input optical signal, the sensed optical signal having a resonant wavelength which varies according to a concentration of a biomaterial; and
  a plurality of spectrum ring resonators optically connected to the bio-sensing ring resonator, the plurality of spectrum ring resonators configured to extract a plurality of output optical signals from the sensed optical signal, each output optical signal having a different wavelength.

19. The optical biosensor of claim 18, further comprising:
  a plurality of detectors configured to provide information to indicate intensities of the plurality of output optical signals by transforming the plurality of output optical signals into electrical signals.

20. A bio-sensing system comprising:
  a fluidic channel via which a biomaterial flows; and
  a biosensor chip configured to sense at least one of whether a biomaterial exists and a concentration of the biomaterial, based on optical characteristics of the biomaterial, and output an electrical signal based on the sensing, wherein the biosensor chip includes,
    an opening adjacent to the fluidic channel;
    a bio-sensing unit including a first ring resonator configured to generate a sensed optical signal from an input optical signal,
    a wavelength of the sensed optical signal varying according to at least one of whether the biomaterial exists and the concentration of the biomaterial; and
  a spectrometer including a plurality of second ring resonators optically coupled to the first ring resonator, the plurality of second ring resonators having different resonant wavelengths, the spectrometer configured to generate a plurality of output optical signals by passing the sensed optical signal through the plurality of ring resonators, the plurality of output optical signals having intensities that vary based on the biomaterial.

21. The bio-sensing system of claim 20, wherein the bio-sensor chip further comprises: a detecting unit configured to transform the plurality of output optical signals into electrical signals based on the intensities.

22. A method of fabricating an optical biosensor, the method comprising:
forming a cladding layer on a substrate; forming a core layer on the cladding layer; and
patterning the core layer to obtain a bio-sensing ring resonator, a plurality of spectrum ring resonators, and a plurality of optical waveguides, at least one of the plurality of optical waveguides configured to optically couple the bio-sensing ring resonator and the plurality of spectrum ring resonators, the plurality of spectrum ring resonators having different resonant wavelengths.

23. The method of claim 22, further comprising:
forming a plurality of detectors on the substrate before the cladding layer is formed on the substrate.

24. The method of claim 22, wherein the plurality of optical waveguides comprise:
a first optical waveguide configured to receive an input optical signal and provide the input optical signal to the bio-sensing ring resonator as a sensed optical signal;
a second optical waveguide configured to receive the sensed optical signal from the bio-sensing ring resonator and provide the sensed optical signal to the plurality of spectrum ring resonators signals; and
a plurality of third optical waveguides configured to receive output optical signals from the plurality of spectrum ring resonators.

25. The method of claim 24, further comprising: forming a plurality of detectors at one end of the plurality of third optical waveguides.

26. An optical biosensor comprising:
a substrate having a biosensing unit and a spectrometer located thereon, the bio-sensing unit including a first ring resonator configured to generate a sensed optical signal based on a biomaterial, and the spectrometer including a plurality of second ring resonators optically coupled to the first ring resonator, the plurality of second ring resonators configured to divide the sensed optical signal into a plurality of output optical signals that each have a different wavelength.

27. The optical biosensor of claim 26, wherein
the first ring resonator is configured to receive an input optical signal from a first optical waveguide and provide a sensed optical signal to a second optical waveguide, and
the first ring resonator is exposed to the biomaterial via an opening such that a wavelength of the sensed optical signal varies based on a wavelength of the biomaterial.

28. The optical biosensor of claim 27, wherein
the plurality of second ring resonators have different resonant wavelengths,
the plurality of second ring resonators are configured to generate a plurality of output optical signals from the sensed optical signal, and
the plurality of output optical signals have intensities that vary based on the biomaterial.

29. The optical biosensor of claim 28, further comprising:
a detecting unit having a plurality of photo detectors configured to generate a plurality of electrical signals based on the intensities; and
a signal processor configured to determine at least one of a presence and a concentration of the biomaterial based on the electrical signals.

30. A biosensing system comprising:
the optical biosensor of claim 26; and
a fluidic channel configured to receive the biomaterial.

31. The optical biosensor of claim 16, wherein the signal processor is configured to combine the plurality of output optical signals by connecting Gaussian peaks thereof to form an output waveform corresponding to a bandwidth of the sensed optical signal.

32. The optical biosensor of claim 1, wherein the bio-sensing unit is a first optical stage that generates the sensed optical signal and the spectrometer is a second optical stage that receives the sensed optical signal from the first optical stage and generates the plurality of output optical signals from the sensed optical signal.

* * * * *